US009095136B2

(12) United States Patent
Helmke et al.

(10) Patent No.: US 9,095,136 B2
(45) Date of Patent: Aug. 4, 2015

(54) 2-IODO IMIDAZOLE-DERIVATIVES

(71) Applicant: BAYER INTELLECTUAL PROPERTY GMBH, Monheim (DE)

(72) Inventors: Hendrik Helmke, Liederbach (DE); Sebastian Hoffmann, Neuss (DE); Carl Friedrich Nising, Leverkusen (DE); Alexander Sudau, Langenfeld (DE); Tomoki Tsuchiya, Lyons (FR); Jürgen Benting, Leichlingen (DE); Peter Dahmen, Neuss (DE); Ulrike Wachendorff-Neumann, Neuwied (DE); David Bernier, Lyons (FR); Stephane Brunet, Saint André de Corcy (FR); Marie-Claire Grosjean-Cournoyer, Curis au Mont d'Or (FR); Hélène Lachaise, Lyons (FR); Philippe Rinolfi, Châtillon d'Azergues (FR)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/360,007

(22) PCT Filed: Nov. 23, 2012

(86) PCT No.: PCT/EP2012/073427
§ 371 (c)(1),
(2) Date: May 22, 2014

(87) PCT Pub. No.: WO2013/076228
PCT Pub. Date: May 30, 2013

(65) Prior Publication Data
US 2014/0336232 A1    Nov. 13, 2014

(30) Foreign Application Priority Data

Nov. 25, 2011  (EP) .................................... 11190683

(51) Int. Cl.
*A01N 43/50* (2006.01)
*C07D 233/68* (2006.01)
*C07D 405/06* (2006.01)

(52) U.S. Cl.
CPC .............. *A01N 43/50* (2013.01); *C07D 233/68* (2013.01); *C07D 405/06* (2013.01)

(58) Field of Classification Search
CPC ..... A01N 43/50; C07D 233/68; C07D 405/06
See application file for complete search history.

(56) References Cited

U.S. PATENT DOCUMENTS

| 4,118,461 | A |   | 10/1978 | Miller et al. |
| 4,532,341 | A |   | 7/1985  | Holmwood et al. |
| 4,626,595 | A |   | 12/1986 | Holmwood et al. |
| 4,723,984 | A |   | 2/1988  | Holmwood et al. |
| 4,789,672 | A |   | 12/1988 | Holmwood et al. |
| 4,871,390 | A |   | 10/1989 | Holmwood et al. |
| 4,897,107 | A |   | 1/1990  | Holmwood et al. |
| 4,904,298 | A |   | 2/1990  | Holmwood et al. |
| 4,911,746 | A |   | 3/1990  | Holmwood et al. |
| 4,913,727 | A |   | 4/1990  | Stroech et al. |
| 4,929,735 | A |   | 5/1990  | Reiser et al. |
| 4,980,488 | A |   | 12/1990 | Stroech et al. |
| 4,988,819 | A |   | 1/1991  | Stroech et al. |
| 4,990,677 | A |   | 2/1991  | Stroech et al. |
| 5,034,052 | A |   | 7/1991  | Stroech et al. |
| 5,084,465 | A | * | 1/1992  | Cuomo et al. ................. 514/341 |
| 5,097,047 | A |   | 3/1992  | Stroech et al. |
| 5,099,040 | A |   | 3/1992  | Rosen et al. |
| 5,162,357 | A |   | 11/1992 | Seele et al. |
| 5,256,683 | A |   | 10/1993 | Hutt et al. |
| 5,288,883 | A | * | 2/1994  | Scherkenbeck et al. ...... 549/563 |
| 5,789,430 | A |   | 8/1998  | Jautelat et al. |
| 6,114,539 | A | * | 9/2000  | Jautelat et al. ............. 548/323.5 |

FOREIGN PATENT DOCUMENTS

| CA | 2011087 C   |   | 12/2000 |
| DE | 3537817 A1  |   | 4/1987 |
| DE | 4027608 A1  |   | 3/1992 |
| EP | 0044605 A1  | * | 1/1982 |
| EP | 0087148 A1  |   | 8/1983 |
| EP | 0040345 B1  |   | 7/1984 |
| EP | 0165775 A1  | * | 12/1985 |
| EP | 0297345 A1  |   | 1/1989 |
| EP | 0319481 A1  |   | 6/1989 |
| EP | 0421125 A2  |   | 8/1990 |

(Continued)

OTHER PUBLICATIONS

Sosnowski et al., "A Comparison of Microwave-Accelerated and Conventionally Heated Iodination Reactions of Some Arenes and Heteroarenes, Using ortho-Periodic Acid as the Oxidant" Molecules. vol. 10: 401-406, 2005.
Devadas et al., J. Med. Chem. vol. 40: 2609-2625, 1997.
Sikorski et al., "Selective Peptidic and Peptidomimetic nhibitors of Candida albicans MyristoylCoA: Protein N-Myristoyltransferase: A New Approach to Antifungal Therapy" Bioplymers. vol. 43: 43-71, 1997.
International Search Report received in PCT/EP2012/073427 dated Mar. 28, 2013.

(Continued)

*Primary Examiner* — Joseph Kosack
*Assistant Examiner* — Amanda L Aguirre
(74) *Attorney, Agent, or Firm* — Miles and Stockbridge

(57) ABSTRACT

The present invention relates to novel 2-iodoimidazole derivatives, to processes for preparing these compounds, to compositions comprising these compounds and to their use as biologically active compounds, in particular for controlling harmful microorganisms in crop protection and in the protection of materials and as plant growth regulators.

10 Claims, No Drawings

(56) References Cited

FOREIGN PATENT DOCUMENTS

| | | |
|---|---|---|
| EP | 0412849 A2 | 2/1991 |
| EP | 0386557 B1 | 6/1992 |
| EP | 0793657 B1 | 11/1995 |
| EP | 0412849 B1 | 12/1995 |
| EP | 0378953 B1 | 6/1996 |
| WO | 8706430 A1 | 11/1987 |
| WO | WO2012009678 A1 * | 1/2012 |

OTHER PUBLICATIONS

J. Med. Chem 1997, 40, 2609-2625, discussed on p. 1, 2nd paragraph of specification.

Biopolymers 1997, 43, 43-71, discussed on p. 1, 2nd paragraph of specification.

* cited by examiner

2-IODO IMIDAZOLE-DERIVATIVES

CROSS REFERENCE TO RELATED APPLICATIONS

This application is a §371 National Stage Application of PCT/EP2012/073427, filed Nov. 23, 2012, which claims priority to EP 11190683.0, filed Nov. 25, 2011.

BACKGROUND

1. Field of the Invention

The present invention relates to novel 2-iodoimidazole derivatives, to processes for preparing these compounds, to compositions comprising these compounds and to their use as biologically active compounds, in particular for controlling harmful microorganisms in crop protection and in the protection of materials and as plant growth regulators.

2. Description of Related Art

It is already known that certain 2-iodoimidazole derivatives can be used as fungicides in crop protection or as antimycotics against dermatophytes (cf. WO 87/06430; J. Med. Chem. 1997, 40, 2609-2625; Biopolymers 1997, 43, 43-71). In addition, other imidazole derivatives substituted in the 2-position by halogen are known as pesticides (cf. EP-A 0 412 849).

Since the ecological and economical demands made on modern active compounds, for example fungicides, are increasing constantly, for example with respect to activity spectrum, toxicity, selectivity, application rate, formation of residues and favourable manufacture, and there can furthermore be problems, for example, with resistances, there is a constant need to develop novel fungicidal compositions which, at least in some areas, have advantages over the known ones.

SUMMARY

This invention now provides novel 2-iodoimidazole derivatives of the formula (I)

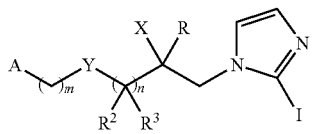

(I)

in which
X represents $OR^1$, CN or hydrogen,
Y represents O, S, SO, $SO_2$, —$CH_2$— or a direct bond,
m represents 0 or 1,
n represents 0 or 1,
R represents in each case optionally substituted alkyl, alkenyl, alkynyl, cycloalkyl or aryl,
$R^1$ represents hydrogen, optionally substituted alkylcarbonyl or trialkylsilyl,
$R^2$ represents hydrogen, halogen or optionally substituted alkyl,
$R^3$ represents hydrogen, halogen or optionally substituted alkyl,
$R^2$ and $R^3$ together may furthermore represent optionally substituted $C_2$-$C_5$-alkylene,
R and $R^2$ together may furthermore represent optionally substituted $C_2$-$C_5$-alkylene,
R and $R^1$ together may furthermore represent in each case optionally halogen-, alkyl- or haloalkyl-substituted $C_1$-$C_4$-alkylene or $C_1$-$C_4$-alkyleneoxy, where the oxygen of this group is joined to R so as to form an optionally substituted tetrahydrofuran-2-yl, 1,3-dioxetan-2-yl, 1,3-dioxolan-2-yl, 1,3-dioxan-2-yl or 1,3-dioxepan-2-yl ring,
$R^1$ and $R^2$ may furthermore represent a direct bond if n represents 1,
Y and $R^3$ together may furthermore form a double bond if m and n both represent 1,
A represents optionally substituted aryl or optionally substituted heteroaryl,
and their agrochemically active salts.

The salts obtainable likewise have fungicidal and/or plant growth regulatory properties.

DETAILED DESCRIPTION OF A PREFERRED EMBODIMENT

The heterocyclic thio-substituted alkanol derivatives which can be used in accordance with the invention are defined in general terms by the formula (I). Preferred radical definitions for the formulae specified above and hereinafter are given below. These definitions apply equally to the end products of the formula (I) and to all intermediates (see also below under "Illustrations of the processes and intermediates").

X preferably represents $OR^1$.
Y preferably represents O.
Y likewise preferably represents —$CH_2$—.
Y likewise preferably represents a direct bond.
Y likewise preferably represents S or $SO_2$.
Y particularly preferably represents oxygen.
Y likewise particularly preferably represents $CH_2$—.
Y likewise particularly preferably represents a direct bond.
m preferably represents 0.
m likewise preferably represents 1.
n preferably represents 0.
n likewise preferably represents 1.
R preferably represents in each case optionally branched $C_3$-$C_7$-alkyl, $C_1$-$C_8$-haloalkyl, $C_2$-$C_7$-alkenyl, $C_2$-$C_7$-haloalkenyl, $C_2$-$C_7$-alkynyl, $C_2$-$C_7$-haloalkynyl, $C_1$-$C_4$-alkoxy-$C_1$-$C_3$-alkyl, $C_1$-$C_4$-haloalkoxy-$C_1$-$C_3$-alkyl, tri($C_1$-$C_3$-alkyl)silyl-$C_1$-$C_3$-alkyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-haloalkylthio-, $C_1$-$C_4$-alkylthio- or phenoxy-substituted (where phenoxy may in turn be substituted by halogen or $C_1$-$C_4$-alkyl) $C_3$-$C_7$-cycloalkyl or $C_3$-$C_7$-cycloalkyl-$C_1$-$C_3$-alkyl where any substitution is on the cycloalkyl moiety, and optionally mono- to tri-halogen- or —$C_1$-$C_4$-alkyl-substituted phenyl.
R particularly preferably represents in each case optionally branched $C_3$-$C_6$-alkyl, $C_1$-$C_6$-haloalkyl, $C_3$-$C_5$-alkenyl, $C_3$-$C_5$-haloalkenyl, $C_3$-$C_5$-alkynyl, $C_3$-$C_5$-haloalkynyl, $C_1$-$C_3$-alkoxy-$C_1$-$C_2$-alkyl, $C_1$-$C_3$-haloalkoxy-$C_1$-$C_2$-alkyl, tri($C_1$-$C_2$-alkyl)silyl-$C_1$-$C_2$-alkyl, in each case optionally halogen-, $C_1$-$C_4$-alkyl-, $C_1$-$C_4$-haloalkyl-, $C_1$-$C_4$-haloalkoxy-, $C_1$-$C_4$-alkoxy-, $C_1$-$C_4$-haloalkylthio-, $C_1$-$C_4$-alkylthio- or phenoxy-substituted (where phenoxy may in turn be substituted by fluorine, chlorine, bromine or $C_1$-$C_4$-alkyl) $C_3$-$C_6$-cycloalkyl or $C_3$-$C_6$-cycloalkyl-$C_1$-$C_2$-alkyl where any substitution is on the cycloalkyl moiety, and optionally mono- to tri-halogen- or —$C_1$-$C_4$-alkyl-substituted phenyl.
R very particularly preferably represents tert-butyl, isopropyl, 1,1,2,2-tetrafluoroethoxymethyl, trimethylsilylmethyl, 1-chlorocyclopropyl, 1-fluorocyclopropyl, 1-methylcyclopropyl, 1-methoxycyclopropyl, 1-methylthiocyclopropyl, 1-trifluoromethylcyclopropyl, 1-phenoxycyclopropyl, 1-(2-chlorophenoxy)cyclopropyl, 1-(2-fluorophenoxy)cyclopropyl, 1-(4-fluorophenoxy)cyclopropyl, 1-(2,4-difluorophenoxy)cyclopropyl, (3E)-4-chloro-2-methylbut-3-en-2-yl, $C_1$-$C_4$-haloalkyl, cyclopropylmethyl, 1-cyclopropylethyl, 2-cyclopropylethyl, 1-fluorophenyl, 4-chloro-2-fluorophenyl, 2,4-difluorophenyl.

$R^1$ preferably represents hydrogen, ($C_1$-$C_3$-alkyl)carbonyl, ($C_1$-$C_3$-haloalkyl)carbonyl or tri($C_1$-$C_3$-alkyl)silyl.

$R^1$ particularly preferably represents hydrogen, methylcarbonyl or trimethylsilyl.

$R^1$ very particularly preferably represents hydrogen.

$R^2$ preferably represents hydrogen, fluorine, chlorine, bromine, iodine, $C_1$-$C_4$-alkyl or $C_1$-$C_4$-haloalkyl.

$R^2$ particularly preferably represents hydrogen, fluorine, chlorine, methyl, ethyl or trifluoromethyl.

$R^2$ very particularly preferably represents hydrogen or methyl.

$R^3$ preferably represents hydrogen, fluorine, chlorine, bromine, iodine, $C_1$-$C_4$-alkyl or $C_1$-$C_4$-haloalkyl.

$R^3$ particularly preferably represents hydrogen, fluorine, chlorine, methyl, ethyl or trifluoromethyl.

$R^3$ very particularly preferably represents hydrogen or methyl.

$R^2$ and $R^3$ together furthermore preferably represent straight-chain or branched and optionally halogen-, in particular fluorine-, chlorine- or bromine-, substituted $C_2$-$C_5$-alkylene.

$R^2$ and $R^3$ together furthermore particularly preferably represent —$(CH_2)_2$—, —$(CH_2)_4$—, —$(CH_2)_5$— or —$(CH_2)CH(CH_3)$—.

R and $R^2$ together furthermore preferably represent straight-chain or branched and optionally halogen- or $C_1$-$C_4$-alkyl-, in particular fluorine-, chlorine-, bromine- or methyl-, substituted $C_2$-$C_5$-alkylene.

R and $R^2$ together furthermore particularly preferably represent —$(CH_2)_2$—, —$(CH_2)_4$—, —$(CH_2)_5$—, —$(CH_2)_2C(CH_3)_2$—, —$C(CH_3)_2(CH_2)_2$— or —$(CH_2)CH(CH_3)$—.

R and $R^2$ together furthermore very particularly preferably represent —$(CH_2)_2$—.

R and $R^1$ together furthermore preferably represent optionally fluorine-, chlorine-, bromine-, $C_1$-$C_4$-alkyl- or $C_1$-$C_4$-haloalkyl-substituted —$(CH_2)_3$—, —$CH_2O$—, —$(CH_2)_2O$—, —$(CH_2)_3O$—, where the oxygen of this group is in each case attached to R, such that an optionally substituted tetrahydrofuran-2-yl, 1,3-dioxetan-2-yl, 1,3-dioxolan-2-yl or 1,3-dioxan-2-yl ring is formed.

R and $R^1$ together furthermore particularly preferably represent optionally methyl-, ethyl-, n-propyl-, n-butyl-substituted —$(CH_2)_2O$—, where the oxygen of this group is attached to R, such that an optionally substituted 1,3-dioxolan-2-yl is formed.

$R^1$ and $R^2$ may furthermore preferably represent a direct bond if n represents 1, A preferably represents unsubstituted or mono- to tri-$Z^1$-substituted phenyl, where $Z^1$ represents halogen, cyano, nitro, OH, SH, C(alkyl)(=NOalkyl), $C_3$-$C_7$-cycloalkyl, $C_3$-$C_6$-cycloalkyl-$C_1$-$C_2$-alkyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulphinyl, $C_1$-$C_4$-alkylsulphonyl, $C_1$-$C_4$-haloalkylsulphonyl, $C_1$-$C_4$-alkylsulphonyloxy, formyl, $C_2$-$C_5$-alkylcarbonyl, $C_2$-$C_5$-haloalkylcarbonyl, $C_2$-$C_5$-alkoxycarbonyl, $C_2$-$C_5$-haloalkoxycarbonyl, $C_3$-$C_6$-alkenyloxy, $C_3$-$C_6$-alkynyloxy, $C_2$-$C_5$-alkylcarbonyloxy, $C_2$-$C_5$-haloalkylcarbonyloxy, trialkylsilyl, or represents in each case optionally halogen-, $C_1$-$C_4$-alkyl-, $C_1$-$C_4$-haloalkyl-, $C_1$-$C_4$-alkoxy- or $C_2$-$C_4$-alkylcarbonyl-monosubstituted phenyl, phenoxy or phenylthio.

A particularly preferably represents unsubstituted or mono- to tri-$Z^1$-substituted phenyl, where $Z^1$ represents halogen, cyano, nitro, C($C_1$-$C_5$-alkyl)(=NO($C_1$-$C_5$-alkyl)), $C_3$-$C_6$-cycloalkyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_2$-$C_4$-alkenyl, $C_2$-$C_4$-alkynyl, $C_1$-$C_4$-alkylsulphinyl, $C_1$-$C_4$-alkylsulphonyl, $C_2$-$C_5$-alkylcarbonyl, $C_2$-$C_5$-alkoxycarbonyl, $C_3$-$C_6$-alkenyloxy, $C_3$-$C_6$-alkynyloxy, $C_2$-$C_5$-alkylcarbonyloxy, or represents in each case optionally halogen-, $C_1$-$C_4$-alkyl-, $C_1$-$C_4$-haloalkyl-, $C_1$-$C_4$-alkoxy- or $C_2$-$C_4$-alkylcarbonyl monosubstituted phenyl, phenoxy or phenylthio.

A very particularly preferably represents unsubstituted or mono- to tri-$Z^1$-substituted phenyl, where Z represents halogen, cyano, nitro, C($C_1$-$C_4$-alkyl)(=NO($C_1$-$C_4$-alkyl)), $C_3$-$C_6$-cycloalkyl, $C_1$-$C_4$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylsulphinyl, $C_1$-$C_2$-alkylsulphonyl, acetyl, methoxycarbonyl, ethoxycarbonyl, methylcarbonyloxy, or in each case optionally halogen-, $C_1$-$C_2$-alkyl-, $C_1$-$C_2$-haloalkyl-, $C_1$-$C_2$-alkoxy-, acetyl-monosubstituted phenyl, phenoxy or phenylthio.

A especially preferably represents unsubstituted or mono- to tri-$Z^1$-substituted phenyl, where $Z^1$ represents fluorine, chlorine, bromine, iodine, cyano, nitro, CH(=NOMe), cyclopropyl, cyclobutyl, cyclopentyl, cyclohexyl, methyl, ethyl, n-propyl, isopropyl, n-, i-, s- or t-butyl, trifluoromethyl, trichloromethyl, difluoromethyl, dichloromethyl, difluorochloromethyl, methoxy, trifluoromethoxy, difluoromethoxy, methylthio, trifluoromethylthio, difluoromethylthio, or in each case optionally fluorine-, chlorine-, bromine-, iodine-, methyl-, ethyl-, trifluoromethyl-, trichloromethyl-, difluoromethyl-, dichloromethyl-, difluorochloromethyl-, methoxy-, acetyl-monosubstituted phenyl, phenoxy or phenylthio.

A likewise preferably represents in each case optionally mono- or poly-$Z^2$-substituted five- or six-membered heteroaryl selected from furyl, thienyl, pyrrolyl, pyrazolyl, imidazolyl, oxazolyl, thiazolyl, isoxazolyl, isothiazolyl, triazolyl, tetrazolyl, oxadiazolyl, thiadiazolyl, pyridinyl, pyridazinyl, pyrimidinyl, pyrazinyl and triazinyl, where $Z^2$ represents halogen, $C_1$-$C_4$-alkyl, $C_1$-$C_4$-alkylthio, $C_1$-$C_4$-alkoxy, $C_1$-$C_4$-haloalkyl, $C_1$-$C_4$-halothioalkyl, $C_1$-$C_4$-haloalkoxy, $C_3$-$C_7$-cycloalkyl or in each case optionally halogen- or $C_1$-$C_4$-alkyl-substituted phenyl, phenoxy or phenylthio.

A likewise particularly preferably represents in each case optionally mono- or poly-$Z^2$-substituted five- or six-membered heteroaryl selected from 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1,2,4-triazol-1-yl, 4H-1,2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl, where $Z^2$ represents halogen, $C_1$-$C_4$-alkyl, $C_1$-$C_2$-alkylthio, $C_1$-$C_2$-alkoxy, $C_1$-$C_2$-haloalkyl, $C_1$-$C_2$-halothioalkyl, $C_1$-$C_2$-haloalkoxy, $C_3$-$C_6$-cycloalkyl, in each case optionally halogen- or $C_1$-$C_4$-alkyl-monosubstituted phenyl or phenoxy.

A likewise very particularly preferably represents in each case optionally mono- or poly-$Z^2$-substituted five- or six-membered heteroaryl selected from 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 2-imidazolyl, 4-imidazolyl, 5-imidazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 1H-1,2,4-triazol-3-yl, 1H-1,2,4-triazol-5-yl, 1H-1,2,4-triazol-1-yl, 1H-tetrazol-1-yl, 1H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, where $Z^2$ represents fluorine, chlorine, bromine, iodine, methyl, ethyl, n-propyl, isopropyl, n-, i-, s- or t-butyl, cyclopropyl, trifluoromethyl, trifluoromethoxy, trifluoromethylthio, trichloromethyl, difluoromethyl, difluoromethoxy, difluoromethylthio, dichloromethyl, difluorochloromethyl, difluorochloromethoxy, $Z^2$ furthermore represents phenyl substituted by fluorine, chlorine or methyl.

The radical definitions and explanations given above in general terms or stated within preferred ranges can, however, also be combined with one another as desired, i.e. including between the particular ranges and preferred ranges. They apply both to the end products and, correspondingly, to the precursors and intermediates. Moreover, individual definitions may not apply.

Preference is given to compounds of the formula (I) in which all radicals in each case have the preferred meanings mentioned above.

Particular preference is given to those compounds of the formula (I) in which all radicals in each case have the abovementioned more preferred definitions.

Very particular preference is given to those compounds of the formula (I) in which all radicals in each case have the abovementioned most preferred definitions.

In the definitions of the symbols given in the above formulae, collective terms were used, which are generally representative of the following substituents:

halogen: (including in combinations such as haloalkyl, haloalkoxy etc.) fluorine, chlorine, bromine and iodine;

alkyl: (including in combinations such as alkylthio, alkoxy etc.) saturated, straight-chain or branched hydrocarbyl radicals having 1 to 8 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl;

haloalkyl: (including in combinations such as haloalkylthio, haloalkoxy etc.) straight-chain or branched alkyl groups having 1 to 8 carbon atoms (as specified above), where some or all of the hydrogen atoms in these groups may be replaced by halogen atoms as specified above, for example $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl;

alkenyl: unsaturated, straight-chain or branched hydrocarbyl radicals having 2 to 8 carbon atoms and one double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

cycloalkyl: monocyclic saturated hydrocarbyl groups having 3 to 8 carbon ring members, such as cyclopropyl, cyclobutyl, cyclopentyl, cyclohexyl, cycloheptyl and cyclooctyl;

aryl: unsubstituted or substituted, aromatic, mono-, bi- or tricyclic ring, for example phenyl, naphthyl, anthracenyl (anthryl), phenanthracenyl (phenanthryl);

hetaryl: unsubstituted or substituted, unsaturated heterocyclic 5- to 7-membered ring containing up to 4 nitrogen atoms or alternatively 1 nitrogen atom and up to 2 further heteroatoms selected from N, O and S: for example 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1,2,4-triazol-1-yl, 4H-1, 2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl.

Illustration of the Processes and Intermediates

The 2-iodoimidazole derivatives of the formula (I) can be prepared in different ways. Initially, the possible processes are shown schematically below. Unless stated otherwise, the radicals are each as defined above.

Scheme 1: Process A (II) → (I)

Scheme 2: Process B (Ia) → (Ib)

$Y^1$ represents S.
$Y^2$ represetns SO or $SO_2$.

Scheme 3: Process C (III)

Scheme 4: Process D (IV) → (I-c)

(I-d)

LG represents a nucleophilically substitutable leaving group, for example chlorine, bromide, iodine, methanesulphonyloxy or 4-methylphenylsulphonyloxy.

Preferred radical definitions for the formulae and equations mentioned above and below have already been given above. These definitions apply not only to the end products of the formula (I) but likewise to all intermediates.

Process A

The imidazole derivatives of the formula (II) required as starting materials when carrying out process A according to the invention are known and can be prepared in a known manner (cf. EP-A 0 040 345, EP-A 0 793 657, EP-A 0 297 345, EP-A 0 421 125, EP-A 0 386 557, EP-A 0 378 953).

The iodinating agents likewise required in the performance of process A according to the invention are known. Possible examples include: elemental iodine or iodine monochloride, N-iodoacetamide, N-iodosuccinimide. Process A according to the invention is performed in the presence of a base. Suitable for this purpose are the customary inorganic or organic bases, preferably alkali metal hydrides such as, for example, sodium hydride or potassium hydride, amides such as sodium amide, sodium bis(trimethylsilyl)amide (Na-HDMS), lithium bis(trimethylsilyl)amide (Li-HDMS), lithium diisopropylamide (LDA) or lithium tetramethylpiperidide (LiTMP), or organometallic compounds such as n-, sec- or tert-butyllithium (n-BuLi, sec-BuLi, tert-BuLi) or phenyllithium. Process A according to the invention is usually carried out in the presence of a diluent at temperatures of from −78° C. to +100° C.

Suitable diluents are preferably ethers such as diethyl ether, dioxane, tetrahydrofuran, 1,2-dimethoxyethane, glycol dimethyl ether or diethylene glycol dimethyl ether, or hydrocarbons such as benzene, xylene or toluene. The reaction according to the invention is preferably performed under inert gas such as especially nitrogen or argon.

Process B

The compounds of the formula (I-a) preparable in the abovementioned processes can be converted further to the target compounds of the general structure (I-b).

For conversion of (I-a), it is possible to use oxidizing agents, especially peroxides or peracids (e.g. hydrogen peroxide or meta-chloroperbenzoic acid).

Process B according to the invention is typically performed in the presence of a diluent, e.g. dichloromethane, at temperatures of −20° C. to +100° C.

Process C

The epoxide derivatives of the formula (III) required as starting materials for carrying out process C according to the invention are known and can be prepared in a known manner (for example DE-A 40 27 608, DE-A 35 37 817).

2-Iodo-1H-imidazole, which is likewise needed for carrying out the process C according to the invention, is commercially available or can be prepared from commercially available precursors by procedures described in the literature (*Molecules* 2005, 10, 401-406).

Process C according to the invention is carried out in the presence of a base. Suitable for this purpose are the customary inorganic or organic bases, preferably alkali metal or alkaline earth metal acetates, carbonates, bicarbonates, hydrides, hydroxides or alkoxides such as, for example, sodium acetate, potassium acetate or calcium acetate, sodium carbonate, potassium carbonate, calcium carbonate or caesium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or isopropoxide, n-, iso-, sec- or tert-butoxide or potassium methoxide, ethoxide, n- or isopropoxide, n-, iso-, sec- or tert-butoxide.

Process C according to the invention is usually carried out in the presence of a diluent at temperatures of from −78° C. to +100° C. Preferred diluents are amides such as, for example, dimethylformamide, dimethylacetamide and N-methylpyrrolidone, and also dimethyl sulphoxide, tetramethylenesulphone and hexamethylphosphoric triamide and DMPU; ketones such as acetone, methyl ethyl ketone, methyl isopropyl ketone or methyl isobutyl ketone. The reaction according to the invention is preferably carried out under inert gas such as, in particular, nitrogen or argon.

Process D

The epoxide derivatives of the formula (IV) required as starting materials for carrying out process D according to the invention are known and can be prepared in a known manner (for example EP-A 0 421 125, EP-A 0 386 557).

2-Iodo-1H-imidazole, which is likewise needed for carrying out the process D according to the invention, is commercially available or can be prepared from commercially available precursors by procedures described in the literature (*Molecules* 2005, 10, 401-406).

Process D according to the invention is carried out in the presence of a base. Suitable for this purpose are the customary inorganic or organic bases, preferably alkali metal or alkaline earth metal acetates, carbonates, bicarbonates, hydrides, hydroxides or alkoxides such as, for example, sodium acetate, potassium acetate or calcium acetate, sodium carbonate, potassium carbonate, calcium carbonate or caesium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or isopropoxide, n-, iso-, sec- or tert-butoxide or potassium methoxide, ethoxide, n- or isopropoxide, n-, iso-, sec- or tert-butoxide. Preference is also given to using pyridine or 4-dimethylaminopyridine, alkali metal amides such as sodium amide and potassium amide.

Preferred reaction accelerators are metal halides such as sodium iodide or potassium iodide, quarternary ammonium salts such as tetrabutylammonium chloride, tetrabutylammonium bromide, tetrabutylammonium iodide or tetrabutylammonium bisulphate, benzyltriethylammonium chloride or benzyltriethylammonium bromide or crown ethers such as 12-crown-4, 15-crown-5, 18-crown-6, dibenzo-18-crown-6 or dicyclohexano-18-crown-6.

Process D according to the invention is usually carried out in the presence of a diluent at temperatures of from −78° C. to +100° C. Preferred diluents are amides such as, for example, dimethylformamide, diethylformamide, dimethylacetamide, diethylacetamide and N-methylpyrrolidone, and also dimethyl sulphoxide, tetramethylenesulphone and hexamethylphosphoric triamide and DMPU. The reaction according to the invention is preferably carried out under inert gas such as, in particular, nitrogen or argon.

The 2-iodoimidazole derivatives of the general formula (I) according to the invention can be converted to acid addition salts or metal salt complexes.

Suitable for producing physiologically acceptable acid addition salts of the compounds of the general formula (I) are preferably the following acids: hydrohalic acids, for example hydrochloric acid and hydrobromic acid, especially hydrochloric acid, and also phosphoric acid, nitric acid, sulphuric acid, mono- and bifunctional carboxylic acids and hydroxycarboxylic acids, for example acetic acid, maleic acid, succinic acid, fumaric acid, tartaric acid, citric acid, salicylic acid, sorbic acid, lactic acid, and sulphonic acids, for example p-toluenesulphonic acid and 1,5-naphthalenedisulphonic acid.

The acid addition salts of the compounds of the general formula (I) can be obtained in a simple manner by customary methods for forming salts, for example by dissolving a compound of the general formula (I) in a suitable inert solvent and adding the acid, for example hydrochloric acid, and can be isolated in a known manner, for example by filtering them off, and can optionally be purified by washing with an inert organic solvent.

For preparation of metal salt complexes of the compounds of the general formula (I), preferred options are salts of metals of main group II to IV and of transition groups I and II and IV to VIII of the Periodic Table, examples of which include copper, zinc, manganese, magnesium, tin, iron and nickel.

Useful anions of the salts include those which are preferably derived from the following acids: hydrohalic acids, for example hydrochloric acid and hydrobromic acid, and also phosphoric acid, nitric acid and sulphuric acid.

The metal salt complexes of compounds of the general formula (I) can be obtained in a simple manner by customary processes, for example by dissolving the metal salt in alcohol, for example ethanol, and adding the solution to the compound of the general formula I. Metal salt complexes can be isolated in a known manner, for example by filtering them off, and can optionally be purified by recrystallization.

The 2-iodoimidazole derivatives which can be used according to the invention may optionally be present as mixtures of different possible isomeric forms, especially of stereoisomers, for example, E and Z isomers, threo and erythro isomers, and optical isomers, but if appropriate also of tautomers. What is claimed are both the E and the Z isomers, and also the threo and erythro, and also the optical isomers, any mixtures of these isomers, and also the possible tautomeric forms.

If appropriate, the compounds of the formula (I) are in particular present in the form of enantiomers:

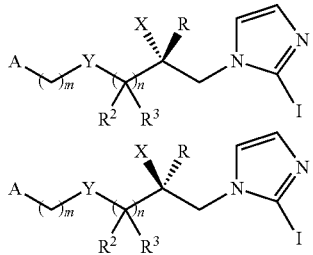

If the substituents $R^2$ and $R^3$ are different, the following diastereomers are optionally present in various mixtures:

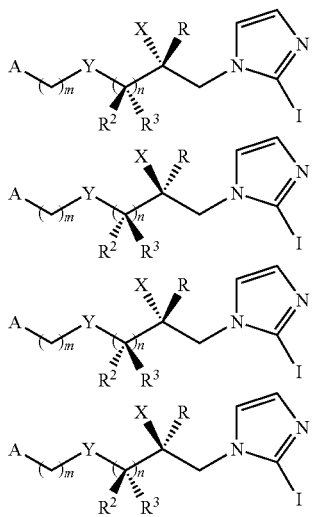

The present invention furthermore relates to a crop protection composition for controlling unwanted microorganisms, in particular unwanted fungi, which comprises the active compounds according to the invention. Said composition is preferably a fungicidal composition which comprises agriculturally suitable auxiliaries, solvents, carriers, surfactants or extenders.

Moreover, the invention relates to a method for controlling unwanted microorganisms, characterized in that the active compounds according to the invention are applied to the phytopathogenic fungi and/or their habitat.

According to the invention, a carrier is a natural or synthetic organic or inorganic substance with which the active compounds are mixed or bonded for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The compositions according to the invention may comprise additional further components, such as, for example, surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkylsulphates, arylsulphonates, protein hydrolysates, lignosulphite waste liquors and methylcellulose. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active compounds can be combined with any solid or liquid additive customarily used for formulation purposes.

The compositions and formulations according to the invention generally comprise between 0.05 and 99% by weight, 0.01 and 98% by weight, preferably between 0.1 and 95% by weight, particularly preferably between 0.5 and 90% of active compound, very particularly preferably between 10 and 70% by weight.

The active compounds or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds with at least one customary extender, solvent or diluent, emulsifier, dispersant, and/or binder or fixative, wetting agent, water repellent, if appropriate desiccants and UV stabilizers and, if appropriate, dyes and pigments, defoamers, preservatives, secondary thickeners, adhesives, gibberellins and also further processing auxiliaries.

The compositions according to the invention include not only formulations which are already ready for use and can be applied with a suitable apparatus to the plant or the seed, but also commercial concentrates which have to be diluted with water prior to use.

The active compounds according to the invention can be present as such or in their (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

The invention furthermore includes a method for treating seed.

The invention further relates to seed which has been treated by one of the methods described in the previous paragraph. The seeds according to the invention are employed in methods for the protection of seed from unwanted microorganisms. In these methods, seed treated with at least one active compound according to the invention is employed.

The active compounds or compositions according to the invention are also suitable for treating seed. A large part of the damage to crop plants caused by harmful organisms is triggered by the infection of the seed during storage or after sowing both during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after sowing or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore also relates to a method for the protection of seed and germinating plants, from attack by phytopathogenic fungi, by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is effected primarily by treating the soil and the above-ground parts of plants with crop protection compositions. Owing to the concerns regarding a possible impact of the crop protection agents on the environment and the health of humans and animals, there are efforts to reduce the amount of active compounds applied.

One of the advantages of the present invention is that the particular systemic properties of the active compounds and compositions according to the invention mean that treatment of the seed with these active compounds and compositions not only protects the seed itself, but also the resulting plants after emergence, from phytopathogenic fungi. In this way, the immediate treatment of the crop at the time of sowing or shortly thereafter can be dispensed with.

It is also considered to be advantageous that the active compounds or compositions according to the invention can be used in particular also for transgenic seed where the plant growing from this seed is capable of expressing a protein which acts against pests. By virtue of the treatment of such seed with the active compounds or compositions according to the invention, merely the expression of the protein, for example an insecticidal protein, can control certain pests. Surprisingly, a further synergistic effect can be observed in this case, which additionally increases the effectiveness for protection against attack by pests.

The compositions according to the invention are suitable for protecting seed of any plant variety which is employed in agriculture, in the greenhouse, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described further below, the treatment of transgenic seed with the active compounds or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species Bacillus, Rhizobium, Pseudomonas, Serratia, Trichoderma, Clavibacter, Glomus or Gliocladium. This heterologous gene preferably originates from Bacillus sp., in which case the gene product is effective against the European corn borer and/or the Western corn rootworm. Particularly preferably, the heterologous gene originates from Bacillus thuringiensis.

Within the context of the present invention, the composition according to the invention is applied to the seed either alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for seed treatment are known to those skilled in the art and are described, for example, in the following documents: U.S. Pat. No. 4,272,417, U.S. Pat. No. 4,245,432, U.S. Pat. No. 4,808,430, U.S. Pat. No. 5,876,739, US 2003/0176428 A1, WO 2002/080675, WO 2002/028186.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Usable with preference are nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed dressing formulations usable in accordance with the invention are all substances usable for such purposes in agrochemical compositions. Dichlorophene and benzyl alcohol hemi-formal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- und Schädlingsbekämp-fungsmittel" [Chemistry of the Crop Protection Compositions and Pesticides], vol. 2, Springer Verlag, 1970, p. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The active compounds or compositions according to the invention have a potent microbicidal activity and can be employed for controlling undesirable microorganisms, such as fungi and bacteria, in crop protection and in the protection of materials.

Fungicides can be used in crop protection for control of Plasmodiophoromycetes, Oomycetes, Chytridiomycetes, Zygomycetes, Ascomycetes, Basidiomycetes and Deuteromycetes.

Bactericides can be used in crop protection for control of Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compounds or compositions according to the invention, which are applied to the seed, the plant or plant parts, the fruit or the soil in which the plants grow.

The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

The fact that the active compounds are well tolerated by plants at the concentrations required for controlling plant diseases allows the treatment of above-ground parts of plants, of propagation stock and seeds, and of the soil.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seeds.

The active compounds according to the invention are suitable for the protection of plants and plant organs, for increasing the harvest yields, for improving the quality of the harvested crop, while being well tolerated by plants, having favourable toxicity to warm-blooded species and being environmentally friendly. They can preferably be used as crop protection agents. They are effective against normally sensitive and resistant species and against all or some stages of development.

Plants which can be treated in accordance with the invention include the following main crop plants: maize, soya bean, cotton, *Brassica* oil seeds such as *Brassica napus* (e.g. Canola), *Brassica rapa*, *B. juncea* (e.g. (field) mustard) and *Brassica carinata*, rice, wheat, sugar beet, sugar cane, oats, rye, barley, millet and sorghum, triticale, flax, grapes and various fruit and vegetables from various botanic taxa, for example Rosaceae sp. (for example pome fruits such as apples and pears, but also stone fruits such as apricots, cherries, almonds and peaches, and berry fruits such as strawberries), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes, potatoes, peppers, aubergines), Liliaceae sp., Compositae sp. (for example lettuce, artichokes and chicory—including root chicory, endive or common chicory), Umbelliferae sp. (for example carrots, parsley, celery and celeriac), Cucurbitaceae sp. (for example cucumbers—including gherkins, pumpkins, watermelons, calabashes and melons), Alliaceae sp. (for example leeks and onions), Cruciferae sp. (for example white cabbage, red cabbage, broccoli, cauliflower, Brussels sprouts, pak choi, kohlrabi, radishes, horseradish, cress and chinese cabbage), Leguminosae sp. (for example peanuts, peas, and beans—for example common beans and broad beans), Chenopodiaceae sp. (for example Swiss chard, fodder beet, spinach, beetroot), Malvaceae (for example okra), Asparagaceae (for example asparagus); useful plants and ornamental plants in the garden and woods; and in each case genetically modified types of these plants.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They may be cultivars, varieties, bio- or genotypes.

The method of treatment according to the invention can be used in the treatment of genetically modified organisms (GMOs), e.g. plants or seeds. Genetically modified plants (or transgenic plants) are plants in which a heterologous gene has been integrated stably into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene present in the genome is also called a transgene. A transgene that is defined by its specific presence in the plant genome is called a transformation or transgenic event.

Depending on the plant species or plant varieties, their location and growth conditions (soils, climate, vegetation period, diet), the treatment according to the invention may also result in superadditive ("synergistic") effects. For example, the following effects exceeding the effects actually to be expected are possible: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processibility of the harvested products.

At certain application rates, the active compounds according to the invention may also have a strengthening effect on plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-fortifying (resistance-inducing) substances shall be understood to mean, in the present context, also those substances or combinations of substances which are capable of stimulating the defence system of plants in such a way that, when subsequently inoculated with unwanted phytopathogenic fungi, the plants treated display a substantial degree of resistance to these unwanted phytopathogenic fungi. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stress factors, i.e. said plants have a better defence against animal and microbial pests, such as against nematodes, insects, mites, phytopathogenic fungi, bacteria, viruses and/or viroids.

Examples of nematode-resistant plants are described, for example, in the following U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 and Ser. No. 12/497,221.

Plants and plant cultivars which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant cultivars which can likewise be treated in accordance with the invention are those plants which are characterized by enhanced yield characteristics. Enhanced yield in these plants may be the result of, for example, improved plant physiology, improved plant growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid effect, which results in generally higher yield, vigour, better health and resistance towards biotic and abiotic stress factors. Such plants are typically produced by crossing an inbred male-sterile parent line (the female parent) with another inbred male-fertile parent line (the male parent). The hybrid seed is typically harvested from the male-sterile plants and sold to growers. Male-sterile plants can sometimes (for example in corn) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are, for example, glyphosate-tolerant plants, i.e. plants which have been made tolerant to the herbicide glyphosate or salts thereof. Plants can be made tolerant to glyphosate by various methods. For example, glyphosate-tolerant plants can be obtained by transforming the plant with a gene which encodes the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a petunia EPSPS (Shah et al., 1986, Science 233, 478-481), a tomato EPSPS (Gasser et al., J. Biol. Chem. 263, 4280-4289) or an *Eleusine* EPSPS (WO 01/66704). It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes. Plants which express EPSPS genes which impart glyphosate tolerance have been described. Plants which express other genes which impart glyphosate tolerance, for example decarboxylase genes, have been described.

Other herbicide-resistant plants are for example plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (for example the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvatedioxygenases are enzymes that catalyse the reaction in which para-hydroxyphenylpyruvate (HPP) is converted to homogentisate. Plants tolerant to HPPD-inhibitors can be transformed with a gene encoding a naturally-occurring resistant HPPD enzyme, or a gene encoding a mutated or chimeric HPPD enzyme, as described in WO 96/38567, WO 99/24585, WO 99/24586, WO 2009/144079, WO 2002/046387 or U.S. Pat. No. 6,768,044. Tolerance to HPPD inhibitors can also be obtained by transforming plants with genes encoding certain enzymes enabling the formation of homogentisate despite the inhibition of the native HPPD enzyme by the HPPD inhibitor. Such plants are described in WO 99/34008 and WO 02/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928. In addition, plants can be made more tolerant to HPPD inhibitors by inserting into the genome thereof a gene which encodes an enzyme which metabolizes or degrades HPPD inhibitors, for example CYP450 enzymes (see WO 2007/103567 and WO 2008/150473).

Further herbicide-resistant plants are plants that have been made tolerant to acetolactate synthase (ALS) inhibitors. The known ALS inhibitors include, for example, sulphonylurea, imidazolinone, triazolopyrimidines, pyrimidinyl oxy(thio) benzoates and/or sulphonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright (*Weed Science* 2002, 50, 700-712). The production of sulphonylurea-tolerant plants and imidazolinone-tolerant plants has been described. Further sulphonylurea- and imidazolinone-tolerant plants have also been described.

Further plants tolerant to imidazolinone and/or sulphonylurea can be obtained by induced mutagenesis, by selection in cell cultures in the presence of the herbicide or by mutation breeding (cf., for example, for soya beans U.S. Pat. No. 5,084, 082, for rice WO 97/41218, for sugar beet U.S. Pat. No. 5,773,702 and WO 99/057965, for lettuce U.S. Pat. No. 5,198,599 or for sunflower WO 01/065922).

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation which imparts such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins compiled by Crickmore et al. (*Microbiology and Molecular Biology Reviews* 1998, 62, 807-813), updated by Crickmore et al. (2005) in the *Bacillus thuringiensis* toxin nomenclature, online at: http://www.lifesci.sussex.ac.uk/Home/Neil_Crickmore/Bt/), or insecticidal portions thereof, for example proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1999141 and WO 2007/107302), or those proteins encoded by synthetic genes as described in U.S. patent application Ser. No. 12/249,016; or 2) a crystal protein from *Bacillus thuringiensis* or a portion thereof which is insecticidal in the presence of a second other crystal protein as *Bacillus thuringiensis* or a portion thereof, such as the binary toxin made up of the Cy34 and Cy35 crystal proteins (Nat. *Biotechnol*. 2001, 19, 668-72; *Applied Environm. Microbiol.* 2006, 71, 1765-1774) or the binary toxin which consists of Cry1A or Cry1F proteins, and the Cry2Aa or Cry2Ab or Cry2Ae proteins (U.S. patent application Ser. No. 12/214,022 and EP08010791.5); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 5) to 7) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102; or 9) a secreted protein from *Bacillus thuringiensis* or *Bacillus cereus* which is insecticidal in the presence of a crystal protein from *Bacillus thuringiensis*, such as the binary toxin made up of the proteins VIP3 and Cry1A or Cry1F (U.S. patent applications 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5); or 10) a protein according to point 9) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein).

Of course, insect-resistant transgenic plants, as used herein, also include any plant comprising a combination of genes encoding the proteins of any one of the abovementioned classes 1 to 10. In one embodiment, an insect-resistant plant contains more than one transgene encoding a protein of any one of the abovementioned classes 1 to 10, to expand the range of target insect species affected or to delay insect resistance development to the plants, by using different proteins insecticidal to the same target insect species but having a different mode of action, such as binding to different receptor binding sites in the insect.

In the present context, an "insect-resistant transgenic plant" additionally includes any plant containing at least one transgene comprising a sequence for production of double-stranded RNA which, after consumption of food by an insect pest, prevents the growth of this pest.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose)polymerase (PARP) gene in the plant cells or plants;

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

4) Transgenic plants or hybrid plants such as onions with particular properties, such as "high soluble solids content", "low pungency" (LP) and/or "long storage" (LS).

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics, and include:

a) plants, such as cotton plants, which contain an altered form of cellulose synthase genes;

b) plants, such as cotton plants, which contain an altered form of rsw2 or rsw3 homologous nucleic acids, such as cotton plants with an increased expression of sucrose phosphate synthase;

c) plants, such as cotton plants, with an increased expression of sucrose synthase;

d) plants, such as cotton plants, wherein the timing of the plasmodesmatal gating at the basis of the fibre cell is altered, for example through downregulation of fibre-selective β-1,3-glucanase;

e) plants, such as cotton plants, which have fibres with altered reactivity, for example through expression of the N-acetyl-glucosaminetransferase gene, including nodC, and chitin synthase genes.

Plants or plant varieties (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics, and include:

a) plants, such as oilseed rape plants, which produce oil having a high oleic acid content;

b) plants, such as oilseed rape plants, which produce oil having a low linolenic acid content;

c) plants, such as oilseed rape plants, which produce oil having a low level of saturated fatty acids.

Plants or plant cultivars (obtained by plant biotechnology methods such as genetic engineering) which may also be treated according to the invention are plants such as potatoes which are virus-resistant, for example to the potato virus Y (SY230 and SY233 events from Tecnoplant, Argentina), or which are resistant to diseases such as potato late blight (e.g. RB gene), or which exhibit reduced cold-induced sweetness (which bear the genes Nt-Inh, II-INV) or which exhibit the dwarf phenotype (A-20 oxidase gene).

Plants or plant cultivars (obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants containing a mutation imparting such altered characteristics, and include plants such as oilseed rape with retarded or reduced seed shattering.

Particularly useful transgenic plants which can be treated according to the invention are plants with transformation events or combinations of transformation events which are the subject of granted or pending petitions for nonregulated status in the USA at the Animal and Plant Health Inspection Service (APHIS) of the United States Department of Agriculture (USDA). Information relating to this is available at any time from APHIS (4700 River Road Riverdale, Md. 20737, USA), for example via the website http://www.aphis.usda.gov/brs/not_reg.html. At the filing date of this application, the petitions with the following information were either granted or pending at the APHIS:

Petition: Identification number of the petition. The technical description of the transformation event can be found in the specific petition document available from APHIS on the website via the petition number. These descriptions are hereby disclosed by reference.

Extension of a petition: Reference to an earlier petition for which an extension of scope or term is being requested.

Institution: Name of the person submitting the petition.

Regulated article: The plant species in question.

Transgenic phenotype: The trait imparted to the plant by the transformation event.

Transformation event or line: The name of the event(s) (sometimes also referred to as line(s)) for which non-regulated status is being requested.

APHIS documents: Various documents which have been published by APHIS with regard to the petition or can be obtained from APHIS on request.

Particularly useful transgenic plants which may be treated according to the invention are plants which comprise one or more genes which encode one or more toxins, and are the transgenic plants which are sold under the following trade names: YIELD GARD® (for example corn, cotton, soyabeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which should be mentioned are corn varieties, cotton varieties and soybean varieties which are available under the following trade names: Roundup Ready® (tolerance to glyphosate, for example corn, cotton, soyabeans), Liberty Link® (tolerance to phosphinothricin, for example oilseed rape), IMI® (tolerance to imidazolinone) and SCS® (tolerance to sulphonylurea, for example corn). Herbicide-resistant plants (plants bred in a conventional manner for herbicide tolerance) which should be mentioned include the varieties sold under the Clearfield® name (for example corn).

Particularly useful transgenic plants which may be treated according to the invention are plants containing transformation events, or a combination of transformation events, and that are listed for example in the databases for various national or regional regulatory agencies (see for example http://ceragmc.org/index.php?evidcode=&hstIDXCode=&gType=&AbbrCode=&atCode=&stCode=&coIDCode=&action=gm_crop_database&mode=Submit and http://gmoinfo.jrc.it/gmp_browse.aspx).

Moreover, in the protection of materials, the active compounds or compositions according to the invention can be employed for protecting industrial materials against attack and destruction by unwanted microorganisms, such as, for example, fungi and insects.

Furthermore, the compounds according to the invention can be used alone or in combinations with other active compounds as antifouling compositions.

Industrial materials in the present context are understood to mean inanimate materials which have been prepared for use in industry. For example, industrial materials which are intended to be protected by active compounds according to the invention from microbial change or destruction can be adhesives, sizes, paper, wallpaper and board, textiles, carpets, leather, wood, paints and plastic articles, cooling lubricants and other materials which can be infested with, or destroyed by, microorganisms. The range of materials to be protected also includes parts of production plants and buildings, for example cooling water circuits, cooling and heating systems, and ventilation and air conditioning systems, which may be impaired by the proliferation of microorganisms. Industrial materials within the scope of the present invention preferably include adhesives, sizes, paper and cardboard, leather, wood, paints, cooling lubricants and heat transfer fluids, more preferably wood. The active compounds or compositions according to the invention may prevent disadvantageous effects, such as rotting, decay, discoloration, decoloration or formation of mould. Moreover, the compounds according to the invention can be employed for protecting objects which come into contact with saltwater or brackish water, in particular hulls, screens, nets, buildings, moorings and signalling systems, against fouling.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The active compounds according to the invention may prevent disadvantageous effects, such as rotting, decay, discoloration, decoloration or formation of mould.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example, *Phytophthora infestans*; *Plasmopara* species, such as, for example, *Plasmopara viticola*; *Pseudoperonospora* species, such as, for example, *Pseudop-*

*eronospora humuli* or *Pseudoperonospora cubensis*; *Pythium* species, such as, for example, *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola* and *M. fijiensis*; *Phaeosphaeria* species, such as, for example, *Phaeosphaeria nodorum*; *Pyrenophora* species, such as, for example, *Pyrenophora teres*; *Ramularia* species, such as, for example, *Ramularia collo-cygni*; *Rhynchosporium* species, such as, for example, *Rhynchosporium secalis*; *Septoria* species, such as, for example, *Septoria apii*; *Typhula* species, such as, for example, *Typhula incarnata*; *Venturia* species, such as, for example, *Venturia inaequalis*;

root and stem diseases caused, for example, by *Corticium* species, such as, for example, *Corticium graminearum*; *Fusarium* species, such as, for example, *Fusarium oxysporum*; *Gaeumannomyces* species, such as, for example, *Gaeumannomyces graminis*; *Rhizoctonia* species, such as, for example *Rhizoctonia solani*; *Tapesia* species, such as, for example, *Tapesia acuformis*; *Thielaviopsis* species, such as, for example, *Thielaviopsis basicola*;

ear and panicle diseases (including corn cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*; *Monographella* species, such as, for example, *Monographella nivalis*; *Septoria* species, such as, for example, *Septoria nodorum*;

diseases caused by smut fungi, such as, for example, *Sphacelotheca* species, such as, for example, *Sphacelotheca reiliana*; *Tilletia* species, such as, for example, *Tilletia caries, T. controversa*; *Urocystis* species, such as, for example, *Urocystis occulta*; *Ustilago* species, such as, for example, *Ustilago nuda, U. nuda tritici*;

fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* and *P. purpurogenum*; *Sclerotinia* species, such as, for example, *Sclerotinia sclerotiorum*;

*Verticilium* species, for example *Verticilium alboatrum*;

seed- and soil-borne rot and wilt diseases, and also diseases of seedlings, caused, for example, by *Fusarium* species, for example *Fusarium culmorum*; *Phytophthora* species, for example *Phytophthora cactorum*; *Pythium* species, for example *Pythium ultimum*; *Rhizoctonia* species, for example *Rhizoctonia solani*; *Sclerotium* species, for example *Sclerotium rolfsii*;

cancers, galls and witches' broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Taphrina* species, for example *Taphrina deformans*;

degenerative diseases of woody plants caused, for example, by *Esca* species, for example *Phaeomoniella chlamydospora* and *Phaeoacremonium aleophilum* and *Fomitiporia mediterranea*;

diseases of flowers and seeds caused, for example, by *Botrytis* species, for example *Botrytis cinerea*;

diseases of plant tubers caused, for example, by *Rhizoctonia* species, such as, for example, *Rhizoctonia solani*; *Helminthosporium* species, such as, for example, *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Microorganisms capable of degrading or altering the industrial materials include, for example, bacteria, fungi, yeasts, algae and slime organisms. The active compounds according to the invention preferably act against fungi, in particular moulds, wood-discoloring and wood-destroying fungi (Basidiomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

In addition, the active compounds according to the invention also have very good antimycotic activity. They have a very broad antimycotic activity spectrum, especially against dermatophytes and yeasts, moulds and diphasic fungi (for example against *Candida* species, such as *Candida albicans*, *Candida glabrata*), and *Epidermophyton floccosum*, *Aspergillus* species, such as *Aspergillus niger* and *Aspergillus fumigatus*, *Trichophyton* species, such as *Trichophyton mentagrophytes*, *Microsporon* species such as *Microsporon canis* and *audouinii*. The list of these fungi by no means constitutes a restriction of the mycotic spectrum covered, and is merely of illustrative character.

Accordingly, the active compounds according to the invention can be used both in medical and in non-medical applications.

When using the active compounds according to the invention as fungicides, the application rates can be varied within a relatively wide range, depending on the kind of application. The application rate of the active compounds according to the invention is in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The active compounds or compositions according to the invention can thus be employed for protecting plants for a certain period of time after treatment against attack by the pathogens mentioned. The period for which protection is provided extends generally for 1 to 28 days, preferably for 1 to 14 days, particularly preferably for 1 to 10 days, very particularly preferably for 1 to 7 days after the treatment of the plants with the active compounds, or for up to 200 days after a seed treatment.

In addition, by the treatment according to the invention it is possible to reduce the mycotoxin content in the harvested material and the foodstuffs and feedstuffs prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *Fusarium acuminatum*, *F. avenaceum*, *F. crookwellense*, *F. culmorum*, *F. graminearum* (*Gibberella zeae*), *F. equiseti*, *F. fujikoroi*, *F. musarum*, *F. oxysporum*, *F. proliferatum*, *F. poae*, *F. pseudograminearum*, *F. sambucinum*, *F. scirpi*, *F. semitectum*, *F. solani*, *F. sporotrichoides*, *F. langsethiae*, *F. subglutinans*, *F. tricinctum*, *F. verticillioides*, inter alia, and also by *Aspergillus* spec., *Penicillium* spec., *Claviceps purpurea*, *Stachybotrys* spec., inter alia.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as intermediates or precursors for the synthesis of other active compounds.

The active compounds according to the invention interfere with the metabolism of the plants and can therefore also be used as growth regulators.

Plant growth regulators may exert various effects on plants. The effects of the compounds depend essentially on the time of application based on the development stage of the plant and also on the amounts of active compound applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sports facilities, on roadsides, at airports or in orchards. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to inhibit, with growth regulators, the degradation of wanted ingredients, such as, for example, sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

The plants listed can be treated according to the invention in a particularly advantageous manner with the compounds of the general formula (I) and/or the compositions according to the invention. The preferred ranges stated above for the active compounds or compositions also apply to the treatment of these plants. Particular emphasis is given to the treatment of plants with the compounds or compositions specifically mentioned in the present text.

The invention is illustrated by the examples below: However, the invention is not limited to the examples.

PREPARATION EXAMPLES

Preparation of Compound No. 1

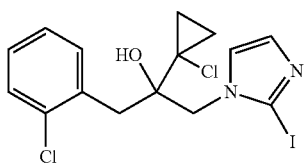 [SMILES: OC(Cc1ccccc1Cl)(Cn1ccnc1I)C1(Cl)CC1]

At room temperature, caesium carbonate (804 mg) was added to a solution of 2-(2-chlorobenzyl)-2-(1-chlorocyclopropyl)oxirane (500 mg) and 2-iodo-1H-imidazole (479 mg) in dimethylformamide (5 ml). The mixture was stirred at 50° C. overnight, and water was then added. The aqueous phase was removed and extracted with ethyl acetate. The combined organic phases were dried over sodium sulphate and concentrated under reduced pressure. The residue was purified by chromatography. This gave 2-(1-chlorocyclopropyl)-1-(2-chlorophenyl)-3-(2-iodo-1H-imidazol-1-yl)propan-2-ol (479 mg).

Preparation of Compound 4

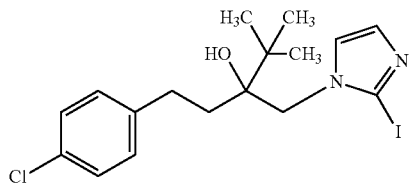 [SMILES: CC(C)(C)C(O)(CCc1ccc(Cl)cc1)Cn1ccnc1I]

Under an atmosphere of argon and at −78° C., 3.44 ml (1.6 M, 5.50 mmol) of n-butyllithium were added to 767 mg (2.50 mmol) of 1-(4-chlorophenyl)-3-(1H-imidazol-1-ylmethyl)-4,4-dimethylpentan-3-ol dissolved in 10 ml of tetrahydrofuran, and the reaction mixture was stirred at 0° C. for 0.5 h. The mixture was then cooled to −78° C., and 698 mg (2.75 mmol) of iodine, dissolved in 2.5 ml of tetrahydrofuran, were then added dropwise and the reaction mixture was heated at room temperature overnight. The next morning, sat. sodium carbonate solution was added at this temperature and the reaction mixture was extracted with ethyl acetate. The combined organic phases were dried over magnesium sulphate, filtered and concentrated. The crude product was then pre-purified by column chromatography (cyclohexane/ethyl acetate 1:1) and subsequently purified by prep. HPLC. This gave 270 mg (24.8%) of the desired product.

Compounds 1, 2, 3, 5 and 18 are obtained in an analogous manner.

Preparation of Compounds 12, 13 and 14

Step 1

Preparation of 1-[1-(2-chlorophenyl)prop-1-en-2-yl]-2,4-difluorobenzene

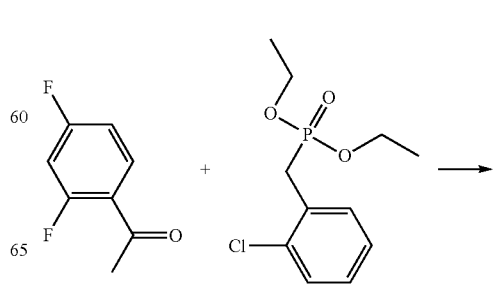

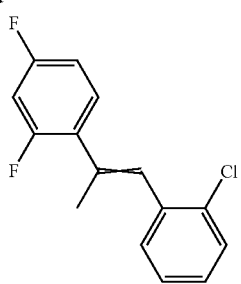

At 3° C., a solution of diethyl 2-chlorobenzylphosphonate (2.00 g, 7.61 mmol) in dry DMF (30 ml) was added to a stirred suspension of sodium hydride (60% by weight suspension in mineral oil, 365 mg, 9.13 mmol; freshly washed with dry heptane) in dry DMF (20 ml). After 1 h of stirring at 3° C., a solution of 2',4'-difluoroacetophenone (1.31 g, 8.37 mmol) in dry DMF (20 ml) was added dropwise. The resulting mixture was stirred at RT for 68 h and then diluted with water and extracted with diethyl ether. The organic phase was dried and concentrated to dryness under reduced pressure, and the residue was purified by chromatography on silica gel, which gave 1-[1-(2-chlorophenyl)prop-1-en-2-yl]-2,4-difluorobenzene as a 93/7 mixture of diastereoisomers [colourless solid, 560 mg, yield 26%; GC/MS: m/z=264 (M+); HPLC/MS: log P$_{(HCOOH)}$=5.05 (major diastereoisomer), 5.34 (minor diastereoisomer)].

Step 2

Preparation of 1-[3-bromo-1-(2-chlorophenyl)prop-1-en-2-yl]-2,4-difluorobenzene

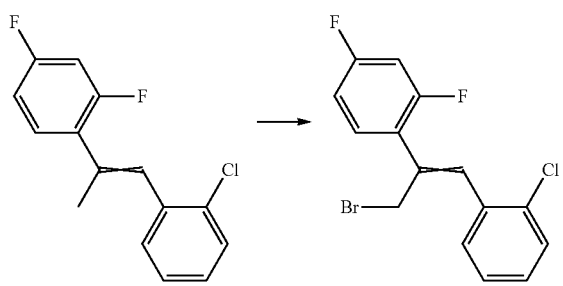 [SMILES: CC(=Cc1ccccc1Cl)c1ccc(F)cc1F ; Fc1ccc(C(=Cc2ccccc2Cl)CBr)c(F)c1]

A stirred solution of 1-[1-(2-chlorophenyl)prop-1-en-2-yl]-2,4-difluorobenzene (680 mg, 2.56 mmol), N-bromosuccinimide (823 mg, 4.62 mmol) and benzoyl peroxide (30 mg) in AcOEt (15 ml) was heated under reflux for 3 h. After cooling to room temperature, the reaction mixture was diluted with AcOEt and washed with water, and the combined organic phases were dried and concentrated to dryness under reduced pressure. Purification by chromatography on silica gel gave 1-[3-bromo-1-(2-chlorophenyl)prop-1-en-2-yl]-2,4-difluorobenzene as a 52/48 mixture of diastereoisomers [colourless oil, 792 mg, yield 85%; GC/MS: m/z=344 (M+); HPLC/MS: log P$_{(HCOOH)}$=4.80 (major diastereoisomer), 5.25 (minor diastereoisomer)].

Step 3

Preparation of 2-(bromomethyl)-3-(2-chlorophenyl)-2-(2,4-difluorophenyl)oxirane

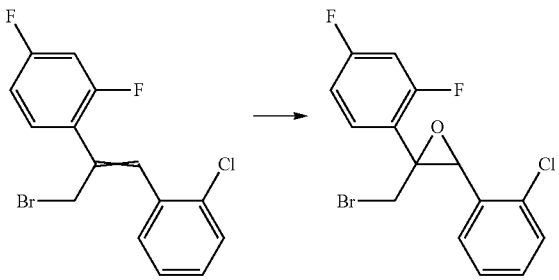 [SMILES: Fc1ccc(C(=Cc2ccccc2Cl)CBr)c(F)c1 ; Fc1ccc(C2(CBr)OC2c2ccccc2Cl)c(F)c1]

Maleic anhydride (2.05 g, 20.9 mmol) and then hydrogen peroxide (35% by weight strength solution, 2.04 g, 20.9 mmol) were added to a stirred solution of 1-[3-bromo-1-(2-chlorophenyl)prop-1-en-2-yl]-2,4-difluorobenzene (720 mg, 2.09 mmol) in acetic acid (20 ml). The reaction mixture was stirred at 40° C. for 24 h, more hydrogen peroxide (35% by weight strength solution, 2.04 g, 20.9 mmol) was then added and the reaction mixture was stirred at 20° C. for 66 h. Excess oxidizing agent was quenched by addition of sat. aq. sodium thiosulphate. The mixture was extracted with dichloromethane, and the organic phase was dried over MgSO$_4$ and concentrated under reduced pressure. Purification of the residue on silica gel gave 2-(bromomethyl)-3-(2-chlorophenyl)-2-(2,4-difluorophenyl)oxirane as a 59/41 mixture of diastereoisomers [316 mg, colourless oil, yield 40%; GC/MS: m/z=279 ([M-Br]$^+$); HPLC/MS: log P$_{(HCOOH)}$=4.61 (major diastereoisomer), 5.00 (minor diastereoisomer)].

Step 4

Preparation of 1-{[3-(2-chlorophenyl)-2-(2,4-difluorophenyl)oxiran-2-yl]methyl}-2-iodo-1H-imidazole

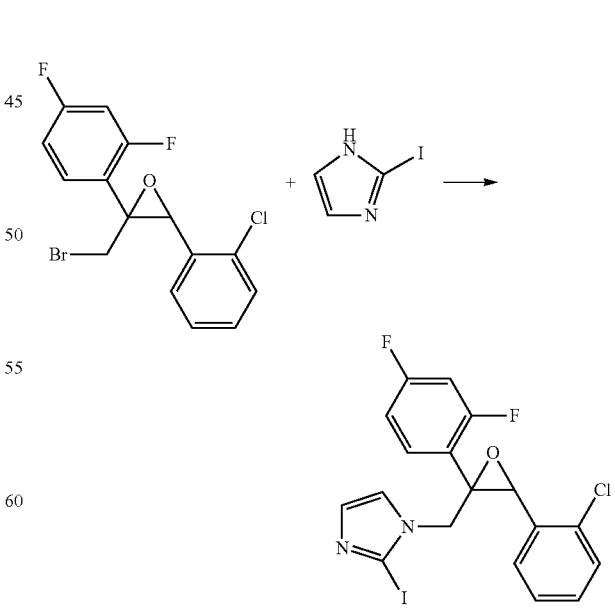

At 3° C., sodium hydride (60% by weight strength dispersion in mineral oil, 56.7 mg, 1.41 mmol) was added to a stirred solution of 2-iodoimidazole (242 mg, 1.25 mmol) in dry DMF (8 ml). The reaction mixture was stirred at room temperature for 20 min, and 2-(bromomethyl)-3-(2-chlorophenyl)-2-(2,4-difluorophenyl)oxirane (300 mg, 0.83 mmol) in dry DMF (4 ml) was then added. The resulting mixture was stirred at 50° C. for 20 h and then at 80° C. for 3 h. After cooling to room temperature, the reaction mixture was diluted with water and extracted with AcOEt, and the extracts were dried and concentrated to dryness under reduced pressure. The filtrates were combined and concentrated to dryness under reduced pressure. Purification of the residue on silica gel gave 1-{[3-(2-chlorophenyl)-2-(2,4-difluorophenyl)oxiran-2-yl]methyl}-2-iodo-1H-imidazole as a 55/45 mixture of diastereoisomers [298 mg, colourless solid, yield 72%; HPLC/MS: m/z=473 (M+H); log P$_{(HCOOH)}$=2.92 (major diastereoisomer), 3.31 (minor diastereoisomer)].

Step 5

Separation of rel-1-{[(2R,3R)-3-(2-chlorophenyl)-2-(2,4-difluorophenyl)oxiran-2-yl]methyl}-2-iodo-1H-imidazole and rel-1-{[(2R,3S)-3-(2-chlorophenyl)-2-(2,4-difluorophenyl)oxiran-2-yl]methyl}-2-iodo-1H-imidazole

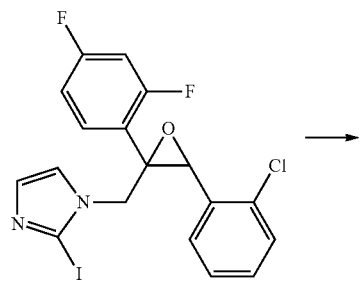

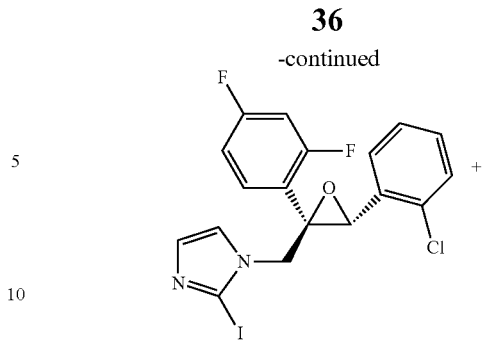

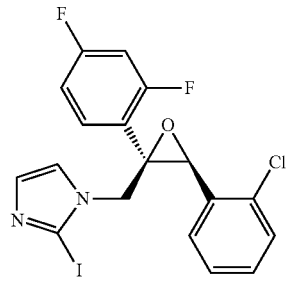

A sample of the abovementioned mixture of diastereoisomers (200 mg) was separated by preparative HPLC (Phenomenex AXIA Gemini C18; 110 A; 10 μm 100×30 mm), which gave rel-1-{[(2R,3R)-3-(2-chlorophenyl)-2-(2,4-difluorophenyl)oxiran-2-yl]methyl}-2-iodo-1H-imidazole as a colourless solid [103 mg, yield 49%; HPLC/MS: m/z=473 (M+H); log P(HCOOH)=2.86] and rel-1-{[(2R,3S)-3-(2-chlorophenyl)-2-(2,4-difluorophenyl)oxiran-2-yl]methyl}-2-iodo-1H-imidazole as a colourless solid [53 mg, yield 25%; HPLC/MS: m/z=473 (M+H); log P$_{(HCOOH)}$=3.23].

Compounds 6 to 17 were obtained in an analogous manner.

The various aspects of the invention are now illustrated with reference to the following Table 1 of exemplary compounds and the following presentation or examples of efficacy.

Table 1 below illustrates in a non-limiting manner examples of compounds according to the invention.

TABLE 1

(I)

| Ex. No. | R | n | X | R2 | R² | R3 | Y | m | A | Stereo-chemistry | logP |
|---|---|---|---|---|---|---|---|---|---|---|---|
| 1 | 1-chlorocyclopropyl | 1 | OH | H | / | H | bond | 0 | 2-chlorophenyl | | 2.35[a]; 3.38[b] |
| 2 | 1-chlorocyclopropyl | 1 | OH | H | / | H | bond | 0 | 2-fluorophenyl | | 2.05[a]; 3.02[b] |
| 3 | 1-(4-fluorophenoxy)cyclopropyl | 0 | OH | / | / | / | bond | 0 | 4-chlorophenyl | | 2.55[a]; 3.55[b] |
| 4 | tert-butyl | 1 | OH | H | / | H | bond | 1 | 4-chlorophenyl | | |
| 5 | 1-(4-fluorophenoxy)cyclopropyl | 0 | OH | / | / | / | bond | 0 | 2,4-difluorophenyl | | |
| 6 | 4-fluorophenyl | 1 | / | / | oxiran-2-yl | H | bond | 0 | 2-chlorophenyl | | 2.73 & 3.08[a] |
| 7 | 4-fluorophenyl | 1 | / | / | oxiran-2-yl | H | bond | 0 | 2-chlorophenyl | rel (R,R) | 2.73[a] |
| 8 | 4-fluorophenyl | 1 | / | / | oxiran-2-yl | H | bond | 0 | 2-chlorophenyl | rel (R,S) | 3.09[a] |
| 9 | 4-chloro-2-fluorophenyl | 1 | / | / | oxiran-2-yl | H | bond | 0 | 2-chlorophenyl | | 3.29 & 3.78[a] |
| 10 | 4-chloro-2-fluorophenyl | 1 | / | / | oxiran-2-yl | H | bond | 0 | 2-chlorophenyl | rel (R,R) | 3.23[a] |
| 11 | 4-chloro-2-fluorophenyl | 1 | / | / | oxiran-2-yl | H | bond | 0 | 2-chlorophenyl | rel (R,S) | 3.7[a] |
| 12 | 2,4-difluorophenyl | 1 | / | / | oxiran-2-yl | H | bond | 0 | 2-chlorophenyl | | 2.92 & 3.31[a] |
| 13 | 2,4-difluorophenyl | 1 | / | / | oxiran-2-yl | H | bond | 0 | 2-chlorophenyl | rel (R,R) | 2.86[a] |
| 14 | 2,4-difluorophenyl | 1 | / | / | oxiran-2-yl | H | bond | 0 | 2-chlorophenyl | rel (R,S) | 3.23[a] |
| 15 | 2-chloro-4-fluorophenyl | 1 | / | / | oxiran-2-yl | H | bond | 0 | 2-chlorophenyl | | 3.13 & 3.57[a] |

TABLE 1-continued

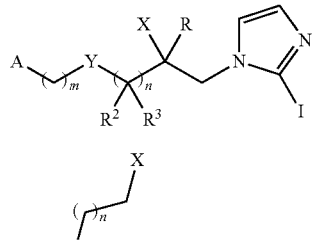

| Ex. No. | R | n | X | R2 | R3 | Y | m | A | Stereo-chemistry | logP |
|---|---|---|---|---|---|---|---|---|---|---|
| 16 | 2-chloro-4-fluorophenyl | 1 | / | / | oxiran-2-yl | H | bond | 0 | 2-chlorophenyl | rel (R,R) | 3.13[a] |
| 17 | 2-chloro-4-fluorophenyl | 1 | / | / | oxiran-2-yl | H | bond | 0 | 2-chlorophenyl | rel (R,S) | 3.68[a] |
| 18 | 1-chlorocyclopropyl | 1 | OH | H | / | H | bond | 0 | 2-chloro-6-iodophenyl | | 3.04[a]; 4[b] |

The log P values were measured according to EEC directive 79/831 Annex V.A8 by HPLC (High Performance Liquid Chromatography) on reversed-phase columns, using the methods below:

[a] Determination by LC-MS took place at a pH of 2.7 with 0.1% formic acid in water and with acetonitrile (contains 0.1% formic acid) as mobile phase using a linear gradient from 10% acetonitrile to 95% acetonitrile.

[b] Determination by LC-MS took place at a pH of 7.8 with 0.001-molar ammonium bicarbonate solution in water as mobile phase using a linear gradient from 10% acetonitrile to 95% acetonitrile.

Calibration was carried out using unbranched alkan-2-ones (having from 3 to 16 carbon atoms) with known log P values (the log P values were determined by the retention times using linear interpolation between two successive alkanones). The lambda maX values were determined in the maxima of the chromatographic signals using the UV spectra from 200 nm to 400 nm.

NMR Data
NMR Data of Selected Examples

The NMR data for selected examples are listed either in conventional form (δ values, number of hydrogen atoms, multiplet splitting) or as NMR peak lists.

Example 1

$^1$H NMR: δ (400 MHz, DMSO-D6)=0.62-0.97 (m, 4H), 3.11 (d, 1H), 3.22 (d, 1H), 4.01 (d, 1H), 4.33 (d, 1H), 5.14 (s, 1H; OH), 6.97 (s, 1H) 7.24-7.32 (m, 2H), 7.37 (s, 1H), 7.40-7.63 (m, 2H) ppm.

Example 2

$^1$H NMR: δ (400 MHz, DMSO-D6)=0.58-0.87 (m, 4H), 2.82 (d, 1H), 3.10 (d, 1H), 4.18 (d, 1H), 4.26 (d, 1H), 5.16 (s, 1H; OH), 6.98 (s, 1H) 7.09-7.31 (m, 3H), 7.39 (s, 1H), 7.45-7.50 (m, 1H) ppm.

Example 3

$^1$H NMR: δ (400 MHz, DMSO-D6)=0.56-0.75 (m, 4H), 4.50 (d, 1H), 4.60 (d, 1H), 5.95 (s, 1H, OH), 6.60-6.64 (m, 2H), 6.86 (s, 1H), 6.96 (t, 2H), 7.26 (s, 1H), 7.32 (d, 2H), 7.49 (d, 2H) ppm.

Example 4

$^1$H NMR: δ (400 MHz, DMSO-D6)=0.99 (s, 9H), 1.05-1.15 (m, 1H), 1.55-1.78 (m, 2H), 2.3-2.4 (m, 1H), 3.94 (d, 1H), 4.13 (d, 1H), 4.58 (s, 1H, OH), 6.97 (d, 2H), 7.00 (s, 1H), 7.27 (d, 2H), 7.45 (s, 1H) ppm.

Example 5

$^1$H NMR: δ (400 MHz, DMSO-D6)=0.75-0.83 (m, 2H), 0.97-1.02 (m, 1H), 1.16-1.22 (m, 1H), 4.52 (d, 2H), 6.17 (s, 1H), 6.63-6.68 (m, 2H), 6.84 (s, 1H), 6.91 (t, 2H), 6.98-7.06 (m, 2H), 7.22 (s, 1H), 7.53-7.60 (m, 1H) ppm.

NMR Peak Lists

When the 1H NMR data for selected examples are noted in the form of 1H NMR peak lists, first the δ value in ppm and then, in round brackets, the signal intensity is listed for each signal peak. The δ value—signal intensity number pairs for different signal peaks are listed with separation from one another by semicolons.

The peak list for one example therefore takes the form of: $δ_1$ (intensity$_1$); $δ_2$ (intensity$_2$); . . . ; $δ_i$ (intensity$_i$); . . . ; $δ_n$ (intensity$_n$)

| NMR peak list table |
|---|
| Example 6, solvent: CDCl3, spectrometer: 499.93 MHz |
| 7.5882 (3.58); 7.5840 (3.84); 7.5740 (3.91); 7.5704 (4.40); 7.5046 (3.90); 7.5019 (3.46); 7.4905 (4.96); 7.4868 (5.12); 7.4748 (0.43); 7.4190 (1.66); 7.4071 (4.92); 7.4044 (4.90); 7.3974 (5.43); 7.3934 (7.76); 7.3828 (4.30); 7.3791 (3.64); 7.3679 (1.40); 7.3645 (1.09); 7.3360 (5.98); 7.3322 (3.47); 7.3255 (7.02); 7.3188 (7.44); 7.3119 (4.02); 7.3083 (6.63); 7.2634 (10.28); 7.2528 (7.03); 7.2509 (6.81); 7.2302 (3.46); 7.2144 (4.24); 7.1321 (4.27); 7.1220 (10.46); 7.1150 (5.26); 7.1044 (4.42); 7.0933 (1.83); 7.0903 (1.77); 7.0779 (3.00); 7.0756 (3.04); 7.0627 (1.89); 7.0596 (1.95); 7.0467 (6.61); 7.0294 (13.12); 7.0215 (14.12); 7.0156 (16.00); 7.0132 (13.79); 7.0007 (2.38); 6.9849 (3.90); 6.9702 (2.46); 6.9472 (3.93); 6.9449 (3.85); 6.9319 (2.17); 6.8528 (4.15); 6.8355 (7.60); 6.8182 (3.71); 4.6028 (3.79); 4.5724 (5.56); 4.4513 (5.71); 4.4210 (4.00); 4.4056 (7.25); 4.3757 (7.78); 4.2513 (12.68); 4.2066 (8.28); 3.6910 (7.87); 3.6611 (7.32); 1.7319 (4.59); −0.0002 (9.27) |

| NMR peak list table |
| --- |
| Example 7, solvent: CDCl3, spectrometer: 499.93 MHz |
| 7.2638 (10.31); 7.2541 (12.32); 7.2513 (12.46); 7.2312 (5.13); 7.2293 (5.23); 7.2153 (6.35); 7.2133 (6.30); 7.1385 (1.04); 7.1327 (7.62); 7.1258 (12.54); 7.1228 (16.00); 7.1195 (5.07); 7.1151 (8.68); 7.1089 (3.77); 7.1046 (8.03); 7.0988 (1.24); 7.0937 (2.60); 7.0902 (2.65); 7.0785 (4.38); 7.0750 (4.39); 7.0632 (2.70); 7.0596 (2.83); 7.0011 (2.46); 6.9993 (2.45); 6.9858 (5.45); 6.9840 (5.37); 6.9710 (3.53); 6.9693 (3.42); 6.9482 (5.87); 6.9447 (5.79); 6.9328 (3.21); 6.9293 (2.88); 6.8589 (1.01); 6.8532 (8.17); 6.8489 (2.57); 6.8396 (3.29); 6.8358 (14.56); 6.8318 (3.10); 6.8225 (2.59); 6.8183 (7.10); 6.8126 (0.88); 4.6035 (7.31); 4.5732 (10.65); 4.4520 (11.35); 4.4216 (7.85); 4.2070 (13.91); 1.7293 (0.47); 1.2533 (0.81); 0.0709 (0.43); 0.0063 (0.45); −0.0002 (10.47); −0.0068 (0.36) |
| Example 8, solvent: CDCl3, spectrometer: 499.93 MHz |
| 7.5170 (3.49); 7.5124 (3.84); 7.5029 (3.79); 7.4987 (4.33); 7.4337 (4.07); 7.4307 (3.32); 7.4194 (5.33); 7.4155 (5.51); 7.4035 (0.39); 7.3510 (1.21); 7.3478 (1.71); 7.3361 (4.99); 7.3330 (4.90); 7.3266 (5.22); 7.3225 (7.63); 7.3185 (4.55); 7.3118 (4.37); 7.3078 (3.67); 7.2969 (1.51); 7.2931 (1.10); 7.2829 (0.38); 7.2704 (0.98); 7.2647 (6.55); 7.2605 (3.26); 7.2542 (7.36); 7.2472 (8.07); 7.2409 (3.97); 7.2367 (7.58); 7.2313 (1.67); 7.2175 (0.63); 7.1910 (9.38); 7.1820 (0.59); 7.1587 (0.32); 7.1424 (0.35); 6.9813 (1.12); 6.9757 (7.22); 6.9716 (2.77); 6.9583 (14.38); 6.9541 (11.83); 6.9517 (13.88); 6.9450 (16.00); 6.9420 (13.16); 4.3344 (8.05); 4.3045 (8.71); 4.1798 (13.19); 3.6193 (9.12); 3.5894 (8.48); 3.0215 (0.35); 2.9148 (0.36); 2.4491 (0.33); 1.6635 (0.51); 1.3576 (7.35); 1.1823 (0.86); −0.0002 (15.97); −0.0654 (0.53); −0.0716 (9.55); −0.0779 (0.55) |
| Example 10, solvent: CDCl3, spectrometer: 400.13 MHz |
| 7.2443 (0.37); 7.2350 (0.47); 7.2313 (0.55); 7.2200 (5.93); 7.2175 (6.15); 7.2000 (7.91); 7.1973 (8.36); 7.1936 (15.71); 7.1842 (13.92); 7.1808 (14.43); 7.1696 (0.38); 7.1146 (0.32); 7.0612 (3.43); 7.0571 (3.64); 7.0477 (13.46); 7.0441 (14.93); 7.0383 (5.89); 7.0227 (3.82); 7.0181 (6.26); 6.9975 (0.98); 6.9895 (1.12); 6.9780 (5.03); 6.9136 (3.32); 6.9115 (3.38); 6.8951 (11.19); 6.8919 (11.68); 6.8756 (6.91); 6.8717 (5.38); 6.8393 (0.36); 6.8278 (6.23); 6.8230 (5.41); 6.8036 (6.18); 6.7988 (5.48); 6.7649 (5.79); 6.7610 (5.79); 6.7456 (4.51); 6.7416 (4.29); 4.6524 (7.01); 4.6145 (8.68); 4.3251 (10.78); 4.3106 (16.00); 4.2873 (8.57); 2.8839 (1.20); 2.8113 (1.01); 1.6934 (0.38); 1.1819 (1.01); 0.0088 (0.69); −0.0002 (17.87); −0.0094 (0.73); −0.0632 (0.37); −0.0714 (9.51); −0.0796 (0.39) |
| Example 11, solvent: CDCl3, spectrometer: 400.13 MHz |
| 7.5243 (1.47); 7.5160 (1.36); 7.5075 (1.08); 7.5055 (1.10); 7.5011 (1.79); 7.4331 (1.61); 7.4282 (1.11); 7.4231 (0.97); 7.4164 (1.47); 7.4102 (2.35); 7.4001 (0.33); 7.3515 (0.35); 7.3429 (2.59); 7.3329 (2.59); 7.3282 (3.82); 7.3191 (4.48); 7.3103 (2.98); 7.3053 (1.74); 7.2925 (0.49); 7.1918 (6.31); 7.0978 (1.65); 7.0892 (2.12); 7.0844 (2.39); 7.0776 (3.33); 7.0645 (2.13); 7.0588 (3.81); 7.0069 (2.59); 7.0022 (2.18); 6.9929 (0.52); 6.9859 (1.59); 6.9815 (1.47); 6.9418 (16.00); 4.4194 (2.74); 4.3817 (3.01); 4.2403 (5.88); 3.6851 (3.77); 3.6475 (3.43); 2.8844 (1.06); 2.8116 (0.94); 1.3437 (0.49); 1.1825 (0.60); −0.0002 (5.48); −0.0717 (4.07) |
| Example 12, solvent: CDCl3, spectrometer: 300.16 MHz |
| 7.6388 (2.30); 7.6250 (2.29); 7.6197 (1.46); 7.6159 (1.75); 7.6131 (1.85); 7.6075 (3.28); 7.5483 (2.61); 7.5411 (1.70); 7.5301 (2.08); 7.5263 (2.34); 7.5175 (4.43); 7.5048 (0.66); 7.4702 (0.37); 7.4623 (1.11); 7.4453 (5.03); 7.4407 (5.70); 7.4276 (7.77); 7.4148 (3.86); 7.4102 (3.08); 7.3932 (0.70); 7.3852 (0.42); 7.3327 (5.29); 7.3295 (5.34); 7.3060 (7.74); 7.2985 (17.31); 7.2940 (13.83); 7.2519 (1.70); 7.2306 (1.89); 7.2237 (3.35); 7.2026 (3.35); 7.1960 (2.07); 7.1701 (5.17); 7.1646 (3.98); 7.1572 (12.71); 7.1528 (12.39); 7.1411 (8.66); 7.1199 (6.60); 7.1139 (5.63); 7.0931 (2.48); 7.0714 (0.36); 7.0483 (13.03); 7.0446 (13.59); 7.0401 (5.03); 7.0279 (0.59); 7.0153 (3.09); 7.0125 (3.03); 6.9896 (6.07); 6.9648 (3.25); 6.9479 (0.32); 6.9367 (15.87); 6.9286 (2.00); 6.9075 (1.90); 6.8999 (2.58); 6.8949 (2.35); 6.8659 (3.83); 6.8596 (7.21); 6.8545 (6.04); 6.8412 (3.36); 6.8336 (6.55); 6.8148 (1.68); 6.8067 (1.28); 6.7613 (1.85); 6.7584 (1.92); 6.7531 (2.20); 6.7320 (3.53); 6.7243 (4.03); 6.7058 (1.69); 6.7033 (1.69); 6.6978 (1.98); 6.6705 (2.93); 6.6624 (2.37); 6.6412 (3.37); 6.6368 (3.70); 6.6291 (2.86); 6.6080 (2.83); 6.5999 (2.41); 4.9593 (0.33); 4.7622 (6.70); 4.7118 (9.01); 4.5042 (4.42); 4.4542 (5.71); 4.4321 (11.04); 4.4218 (16.00); 4.3817 (8.05); 4.3630 (10.69); 3.8130 (7.15); 3.7630 (6.23); 2.9940 (0.89); 2.9213 (0.77); 2.0828 (0.65); 1.6740 (5.17); 1.3406 (0.43); 1.3187 (0.80); 1.3002 (2.60); 1.2714 (0.40); 0.9379 (0.91); 0.9161 (2.78); 0.8927 (1.05) |
| Example 13, solvent: CDCl3, spectrometer: 400.13 MHz |
| 7.3152 (0.38); 7.2929 (5.45); 7.2904 (5.69); 7.2728 (7.40); 7.2703 (7.83); 7.2649 (21.10); 7.2604 (14.20); 7.1267 (4.53); 7.1216 (13.75); 7.1181 (12.28); 7.1084 (7.12); 7.1044 (8.62); 7.0846 (5.19); 7.0680 (2.10); 6.9732 (2.94); 6.9712 (2.99); 6.9538 (5.77); 6.9521 (5.82); 6.9353 (3.12); 6.9334 (3.05); 6.9175 (5.42); 6.8175 (5.50); 6.8019 (4.28); 6.7981 (4.16); 6.7180 (1.73); 6.7158 (1.87); 6.7119 (2.00); 6.7099 (1.99); 6.6960 (3.38); 6.6902 (3.67); 6.6764 (1.61); 6.6743 (1.70); 6.6703 (1.86); 6.6685 (1.80); 6.6262 (2.70); 6.6201 (2.34); 6.6042 (3.14); 6.6009 (3.54); 6.5986 (3.22); 6.5951 (2.80); 6.5792 (2.66); 6.5732 (2.28); 4.7203 (6.59); 4.6825 (8.20); 4.3917 (11.40); 4.3870 (16.00); 4.3541 (8.04); 2.0101 (2.45); 1.7293 (6.61); 0.0079 (0.33); −0.0002 (9.31); −0.0085 (0.33) |
| Example 14, solvent: CDCl3, spectrometer: 400.13 MHz |
| 7.6081 (0.35); 7.5980 (3.06); 7.5904 (2.99); 7.5855 (1.92); 7.5825 (2.13); 7.5808 (2.36); 7.5786 (2.37); 7.5747 (3.83); 7.5669 (0.39); 7.5151 (0.33); 7.5061 (3.70); 7.5014 (2.52); 7.3974 (5.43); 7.4973 (1.95); 7.4908 (3.04); 7.4889 (3.44); 7.4831 (5.49); 7.4724 (0.64); 7.4242 (0.69); 7.4190 (1.49); 7.4055 (5.61); 7.4003 (8.88); 7.3911 (11.48); 7.3825 (6.91); 7.3766 (3.61); 7.3638 (0.93); 7.3580 (0.56); 7.2654 (8.06); 7.2063 (2.08); 7.1904 (2.38); 7.1852 (3.97); 7.1694 (4.00); 7.1644 (2.50); 7.1485 (2.22); 7.0583 (0.32); 7.0154 (6.74); 7.0120 (14.54); 7.0081 (16.00); 7.0046 (6.78); 6.9958 (0.51); 6.8911 (2.11); 6.8850 (2.39); 6.8693 (2.43); 6.8651 (2.89); 6.8635 (3.09); 6.8596 (2.72); 6.8439 (2.04); 6.8378 (2.45); 6.8255 (1.93); 6.8232 (1.88); 6.8193 (1.58); 6.8172 (1.53); 6.8036 (3.28); 6.7976 (2.72); 6.7840 (1.65); 6.7817 (1.64); 6.7778 (1.37); 6.7757 (1.29); 4.4606 (6.14); 4.4230 (6.76); 4.3259 (13.09); 3.7708 (9.14); 3.7332 (8.25); 1.8165 (1.68); −0.0002 (4.90) |
| Example 15, solvent: CDCl3, spectrometer: 499.93 MHz |
| 7.6114 (1.12); 7.6065 (1.15); 7.5972 (1.03); 7.5928 (1.27); 7.5109 (1.28); 7.5077 (0.93); 7.5056 (0.77); 7.4969 (1.57); 7.4926 (1.65); 7.4246 (0.44); 7.4211 (0.64); 7.4098 (1.66); 7.4063 (1.56); 7.4015 (1.71); 7.3963 (2.80); 7.3916 (1.30); 7.3867 (1.39); 7.3825 (1.15); 7.3718 (0.46); 7.3676 (0.35); 7.3053 (5.33); 7.2893 (6.44); 7.2693 |

| NMR peak list table |
|---|
| (8.00); 7.2594 (8.05); 7.2467 (2.94); 7.2313 (2.17); 7.1745 (1.71); 7.1694 (1.63); 7.1579 (1.74); 7.1528 (1.69); 7.1476 (1.45); 7.1355 (2.04); 7.1234 (16.00); 7.1211 (13.34); 7.1106 (5.41); 7.1083 (5.20); 7.0953 (2.87); 7.0923 (2.62); 7.0765 (0.36); 7.0450 (0.38); 7.0323 (3.06); 7.0300 (3.52); 7.0166 (1.16); 6.9553 (0.48); 6.9520 (0.48); 6.9254 (0.40); 6.9032 (3.28); 6.8985 (4.39); 6.8826 (7.46); 6.8703 (6.03); 6.8560 (3.08); 6.8169 (0.35); 6.8144 (0.32); 6.5919 (3.14); 6.5767 (2.81); 4.8481 (3.01); 4.8180 (3.32); 4.5801 (6.05); 4.5391 (0.55); 4.5086 (0.54); 4.4224 (4.41); 4.2811 (3.50); 4.2510 (3.09); 3.9450 (0.54); 3.9151 (0.51); 2.9533 (1.14); 2.8821 (1.01); 1.6010 (7.32); 1.2559 (0.98); 0.1166 (0.35); 0.0698 (0.51); 0.0060 (4.77); −0.0002 (79.00); −0.0067 (2.76); −0.1199 (0.36) Example 16, solvent: CDCl3, spectrometer: 400.13 MHz |
| 7.3366 (0.37); 7.3097 (6.22); 7.2884 (8.29); 7.2768 (10.52); 7.2639 (26.22); 7.2440 (3.78); 7.2388 (3.90); 7.2236 (3.19); 7.2137 (0.72); 7.1775 (0.36); 7.1275 (16.00); 7.1243 (14.73); 7.1147 (6.42); 7.1113 (6.30); 7.0953 (3.52); 7.0915 (3.37); 7.0776 (0.45); 6.9044 (5.02); 6.8844 (9.36); 6.8772 (6.31); 6.8693 (5.86); 6.8562 (4.95); 6.5926 (4.51); 6.5737 (4.03); 4.8555 (5.03); 4.8179 (5.73); 4.5828 (10.23); 4.2828 (6.03); 4.2452 (5.19); 4.1303 (0.55); 4.1124 (0.55); 2.0465 (2.42); 1.6984 (1.66); 1.2774 (0.74); 1.2595 (1.69); 1.2534 (0.96); 1.2417 (0.76); 0.0794 (0.46); 0.0704 (12.64); 0.0612 (0.56); 0.0079 (0.58); −0.0002 (16.22); −0.0084 (0.69) Example 17, solvent: CDCl3, spectrometer: 300.16 MHz |
| 7.6662 (0.41); 7.6532 (3.62); 7.6420 (3.19); 7.6376 (2.36); 7.6336 (2.33); 7.6300 (2.73); 7.6278 (2.82); 7.6221 (4.95); 7.5835 (0.40); 7.5675 (0.51); 7.5564 (4.22); 7.5496 (2.69); 7.5428 (2.38); 7.5340 (3.90); 7.5256 (6.57); 7.5124 (1.28); 7.5034 (0.78); 7.4888 (0.42); 7.4834 (0.60); 7.4779 (0.29); 7.4704 (1.96); 7.4533 (6.80); 7.4471 (10.09); 7.4348 (12.02); 7.4231 (7.17); 7.4164 (4.33); 7.3995 (1.08); 7.3916 (0.64); 7.3381 (0.52); 7.3346 (0.55); 7.3295 (0.64); 7.3187 (0.86); 7.2983 (2.07); 7.2205 (5.39); 7.2121 (5.65); 7.1926 (6.02); 7.1872 (6.49); 7.1848 (6.92); 7.1677 (4.95); 7.1589 (6.34); 7.1390 (5.54); 7.0988 (0.55); 7.0903 (0.72); 7.0694 (15.45); 6.9979 (0.73); 6.9926 (0.68); 6.9536 (3.40); 6.9451 (3.23); 6.9267 (4.55); 6.9183 (4.32); 6.8984 (2.76); 6.8899 (2.55); 4.5836 (2.47); 4.5337 (2.92); 4.4616 (16.00); 3.9893 (3.06); 3.9394 (2.64); 2.0825 (0.78); 2.0456 (0.59); 1.6800 (4.07); 1.3192 (0.57); 1.2887 (2.34); 1.2717 (0.54); 0.9147 (0.34); 0.1175 (1.14); 0.1055 (30.77); 0.0933 (1.53) Example 18, solvent: DMSO, spectrometer: 399.95 MHz |
| 7.9020 (6.61); 7.8998 (6.90); 7.8824 (7.07); 7.8801 (7.00); 7.5163 (7.71); 7.5135 (7.99); 7.4963 (8.69); 7.4936 (8.31); 7.3867 (13.40); 7.3837 (13.57); 7.0283 (7.59); 7.0084 (13.90); 6.9387 (16.00); 6.9355 (15.89); 4.7853 (6.55); 4.5763 (6.21); 4.5399 (7.19); 4.1270 (3.47); 4.0907 (3.02); 3.6333 (0.46); 3.5609 (2.99); 3.3223 (98.65); 2.6754 (0.66); 2.6709 (0.91); 2.6663 (0.65); 2.5412 (0.88); 2.5241 (3.34); 2.5108 (52.94); 2.5064 (104.59); 2.5018 (136.90); 2.4973 (98.76); 2.4928 (47.60); 2.3331 (0.68); 2.3285 (0.92); 2.3241 (0.67); 2.0743 (0.69); 1.1589 (1.48); 1.1402 (2.46); 0.9038 (1.36); 0.8954 (1.87); 0.8858 (3.67); 0.8758 (9.17); 0.8617 (10.44); 0.8509 (3.52); 0.8416 (1.74); 0.8328 (1.37); 0.7271 (1.24); 0.7163 (0.79); 0.7051 (3.30); 0.6965 (3.17); 0.6924 (3.87); 0.6865 (3.08); 0.6736 (2.45); 0.6635 (1.36); 0.0079 (2.67); −0.0002 (69.17); −0.0085 (2.37) |

The intensity of sharp signals correlates with the height of the signals in a printed example of an NMR spectrum in cm and shows the true ratios of the signal intensities. In the case of broad signals, several peaks or the middle of the signal and their relative intensities may be shown in comparison to the most intense signal in the spectrum.

Tetramethylsilane and/or, in particular in the case of spectra measured in DMSO, the chemical shift of the solvent was used to calibrate the chemical shift of 1H NMR spectra. Accordingly, the tetramethylsilane peak may be present in the NMR peak lists, but does not have to be present.

The lists of the 1H NMR peaks are similar to the conventional 1H NMR printouts and thus usually contain all peaks listed in conventional NMR interpretations.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-D6 and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

More details about the 1H-NMR peak lists can be found in the Research Disclosure Database Number 564025.

USE EXAMPLES

Example A

*Alternaria* Test (Tomato)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young tomato plants are sprayed with the preparation of active compound at the stated application rate. 1 day after the treatment, the plants are inoculated with a spore suspension of *Alternaria solani* and then remain at 100% rel. humidity and 22° C. for 24 h. The plants then remain at 96% rel. atmospheric humidity and a temperature of 20° C. Evaluation is carried out 7 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 88 |
| 2 | 95 |

Example B

*Sphaerotheca* Test (Cucumber)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young cucumber plants are sprayed with the preparation of active compound at the stated application rate. 1 day after the treatment, the plants are inoculated with a spore suspension of *Sphaerotheca fuliginea*. The plants are then placed in a greenhouse at 70% relative air humidity and a temperature of 23° C. Evaluation is carried out 7 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 80 |
| 2 | 92 |
| 5 | 88 |

Example C

*Pyricularia* Test (Rice)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young rice plants are sprayed with the preparation of active compound at the stated application rate. 1 day after the treatment, the plants are inoculated with an aqueous spore suspension of *Pyricularia oryzae* and then remain at 100% relative atmospheric humidity and 24° C. for 48 h. The plants are then placed in a greenhouse at 80% relative atmospheric humidity and a temperature of 24° C. Evaluation is carried out 7 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 95 |
| 2 | 80 |
| 4 | 80 |
| 5 | 95 |

Example D

*Venturia* Test (Apple)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day. The plants are then placed in a greenhouse at about 21° C. and a relative atmospheric humidity of about 90%. Evaluation is carried out 10 days after the inoculation. 0% means an efficacy which corresponds to that of the control, whereas an efficacy of 100% means that no infection is observed.

In this test, the following compounds according to the invention show, at an active compound concentration of 100 ppm, an efficacy of 70% or more:

| Ex. No. | Eff. % |
|---|---|
| 1 | 100 |
| 8 | 100 |
| 14 | 100 |

Example E

*Uromyces* Test (Bean)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are inoculated with an aqueous spore suspension of the bean rust pathogen *Uromyces appendiculatus* and then remain in an incubation cabin at about 20° C. and 100% relative atmospheric humidity for 1 day. The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

In this test, the following compounds according to the invention show, at an active compound concentration of 10 ppm, an efficacy of 70% or more:

| Ex. No. | Eff. % |
|---|---|
| 1 | 100 |
| 1 | 88 |
| 2 | 91 |
| 2 | 100 |
| 8 | 100 |
| 17 | 75 |

Example F

Phakopsora Test (Soya Beans)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are inoculated with an aqueous spore suspension of the soya bean rust pathogen *Phakopsora pachyrhizi* and then remain in an incubation cabin in the dark at about 24° C. and about 95% relative atmospheric humidity for 24 h. Further incubation takes place at about 24° C. and a relative atmospheric humidity of about 80% using a day/night rhythm of 12 h of light/12 h of darkness. Evaluation is carried out 7 days after the inoculation. 0% means an efficacy which corresponds to that of the control, whereas an efficacy of 100% means that no infection is observed.

In this test, the following compounds according to the invention show, at an active compound concentration of 100 ppm, an efficacy of 70% or more:

| Ex. No. | Eff. % |
|---|---|
| 1 | 98 |
| 8 | 99 |
| 14 | 100 |

Example G

Blumeria graminis Test (Barley)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are dusted with spores of *Blumeria graminis* f.sp. *hordei*. The plants are placed in a greenhouse at a temperature of about 18° C. and a relative air humidity of about 80% to promote the development of mildew pustules. Evaluation is carried out 7 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 100 |
| 2 | 100 |
| 14 | 90 |

Example H

Leptosphaeria nodorum Test (Wheat)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are sprayed with a spore suspension of *Leptosphaeria nodorum*. The plants remain in an incubation cabin at 20° C. and 100% relative atmospheric humidity for 48 hours. The plants are placed in a greenhouse at a temperature of about 22° C. and a relative atmospheric humidity of about 80%. Evaluation is carried out 8 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 100 |
| 2 | 93 |

Example I

Septoria tritici Test (Wheat)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are sprayed with a spore suspension of *Septoria tritici*. The plants remain in an incubation cabin at 20° C. and 100% relative atmospheric humidity for 48 hours. The plants are then placed under a translucent hood at 15° C. and 100% relative atmospheric humidity for a further 60 hours. The plants are placed in a greenhouse at a temperature of about 15° C. and a relative atmospheric humidity of about 80%. Evaluation is carried out 21 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 100 |
| 2 | 86 |
| 12 | 71 |
| 14 | 100 |

Example K

*Pyrenophora teres* Test (Barley)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are sprayed with a spore suspension of *Pyrenophora teres*. The plants remain in an incubation cabin at 20° C. and 100% relative atmospheric humidity for 48 hours. The plants are placed in a greenhouse at a temperature of about 20° C. and a relative atmospheric humidity of about 80%. Evaluation is carried out 8 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 100 |
| 2 | 100 |

Example L

*Puccinia triticina* Test (Wheat)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are sprayed with spores with a spore suspension of *Puccinia triticina*. The plants remain in an incubation cabin at 20° C. and 100% relative atmospheric humidity for 48 hours. The plants are placed in a greenhouse at a temperature of about 20° C. and a relative atmospheric humidity of about 80%.

Evaluation is carried out 8 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 100 |
| 2 | 100 |
| 14 | 100 |

Example M

*Fusarium nivale* (var. *majus*) Test (Wheat)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are sprayed with a spore suspension of *Fusarium nivale* (var. *majus*). The plants are placed in a greenhouse chamber under a translucent incubation hood at 10° C. and 100% relative atmospheric humidity. Evaluation is carried out 5 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 100 |
| 2 | 100 |

Example N

*Blumeria graminis* Test (Barley)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for protective activity, young plants are sprayed with the preparation of active compound at the stated application rate. After the spray coating has dried on, the plants are sprayed with spores with a spore suspension of *Fusarium graminearum*. The plants are placed in a greenhouse chamber under a translucent incubation hood at 22° C. and 100% relative atmospheric humidity. Evaluation is carried out 5 days after the inoculation. 0% means an efficacy which corresponds to that of the control, whereas an efficacy of 100% means that no infection is observed.

In this test, the following compounds according to the invention show, at an active compound concentration of 500 ppm, an efficacy of 70% or more:

| Ex. No. | Eff. % |
|---|---|
| 1 | 100 |
| 2 | 92 |
| 2 | 100 |

Example O

Preventative In Vivo Test with *Alternaria brassicae* (Leaf Spot on Radish)

The active compounds tested are prepared by homogenization in a mixture of acetone/Tween/DMSO and then diluted with water to the desired active compound concentration.

Radish plants (cultivar "Pernod Clair"), sown in a 50/50 peat/pozzolana soil substrate and cultivated at 17° C., are treated at the 2-leaf stage by spraying with the active compound, prepared as above. As a control, plants are treated with the mixture of acetone/Tween/DMSO/water without the active compound.

After 24 hours, the plants are inoculated by spraying the leaves with an aqueous suspension of *Alternaria brassicae* spores. The inoculated radish plants are incubated at 20° C. and a relative atmospheric humidity of 100%.

Evaluation (% efficacy) is carried out 5 days after inoculation in comparison with the control plants. 0% means an efficacy which corresponds to that of the control plants, whereas an efficacy of 100% means that no infection is observed.

In this test, the following compounds according to the invention show, at an active compound concentration of 500 ppm, an efficacy of 70% or more:

| Ex. No | Efficacy % |
|---|---|
| 6 | 75 |
| 8 | 88 |

Example P

Preventative In Vivo Test with *Botrytis cinerea* (Grey Mould)

The active compounds tested are prepared by homogenization in a mixture of acetone/Tween/DMSO and then diluted with water to the desired active compound concentration.

Cucumber plants (cultivar "Vert petit de Paris"), sown in a 50/50 peat/pozzolana soil substrate and cultivated at 24° C., are treated at the Z11 cotyledon stage by spraying with the active compound, prepared as above. As a control, plants are treated with the mixture of acetone/Tween/DMSO/water without the active compound.

After 24 hours, the plants are inoculated by spraying the cotyledons with an aqueous suspension of cryogenically preserved *Botrytis cinerea* spores. The inoculated cucumber plants are incubated at 17° C. and a relative atmospheric humidity of 80%.

Evaluation (% efficacy) is carried out 4-5 days after inoculation in comparison with the control plants. 0% means an efficacy which corresponds to that of the control plants, whereas an efficacy of 100% means that no infection is observed.

In this test, the following compounds according to the invention show, at an active compound concentration of 500 ppm, an efficacy of 70% or more:

| Ex. No | Efficacy % |
|---|---|
| 11 | 92 |
| 14 | 97 |

Example Q

Preventative In Vivo Test with *Phytophthora infestans* (Late Blight of Tomatoes)

The active compounds tested are prepared by homogenization in a mixture of acetone/Tween/DMSO and then diluted with water to the desired active compound concentration.

Tomato plants (cultivar "Rentita"), sown in a 50/50 peat/pozzolana soil substrate and cultivated at 20-25° C., are treated at the Z12 leaf stage by spraying with the active compound, prepared as above. As a control, plants are treated with the mixture of acetone/Tween/DMSO/water without the active compound.

After 24 hours, the plants are inoculated by spraying the leaves with an aqueous suspension of *Phytophthora infestans* spores. The inoculated tomato plants are incubated at 16-18° C. under a humid atmosphere.

Evaluation (% efficacy) is carried out 5 days after inoculation in comparison with the control plants. 0% means an efficacy which corresponds to that of the control plants, whereas an efficacy of 100% means that no infection is observed.

In this test, the following compounds according to the invention show, at an active compound concentration of 500 ppm, an efficacy of 70% or more:

| Ex. No | Efficacy % |
|---|---|
| 1 | 100 |
| 12 | 88 |
| 13 | 98 |

Example R

Preventative In Vivo Test with *Pyrenophora teres* (Net Blotch on Barley)

The active compounds tested are prepared by homogenization in a mixture of acetone/Tween/DMSO and then diluted with water to the desired active compound concentration.

Barley plants (cultivar "Plaisant"), sown in a 50/50 peat/pozzolana soil substrate and cultivated at 22° C. (12 h)/20° C. (12 h), are treated at the 1-leaf stage (height 10 cm) by spraying with the active compound, prepared as above. As a control, plants are treated with the mixture of acetone/Tween/DMSO/water without the active compound.

After 24 hours, the plants are inoculated by spraying the leaves with an aqueous suspension of *Pyrenophora teres* spores. The inoculated barley plants are incubated at 20° C. and a relative atmospheric humidity of 100% for 48 hours and then for 12 days at a relative atmospheric humidity of 80%.

Evaluation (% efficacy) is carried out 12 days after inoculation in comparison with the control plants. 0% means an efficacy which corresponds to that of the control plants, whereas an efficacy of 100% means that no infection is observed.

In this test, the following compounds according to the invention show, at an active compound concentration of 500 ppm, an efficacy of 70% or more:

| Ex. No | Efficacy % |
|---|---|
| 1 | 100 |
| 8 | 79 |

Example S

Preventative In Vivo Test with *Pyricularia oryzae* (Rice Blast)

The active compounds tested are prepared by homogenization in a mixture of acetone/Tween/DMSO and then diluted with water to the desired active compound concentration.

Rice plants (cultivar "Koshihikari"), sown in a 50/50 peat/pozzolana soil substrate and cultivated at 25° C., are treated at the 2-leaf stage (height 10 cm) by spraying with the active compound, prepared as above. As a control, plants are treated with the mixture of acetone/Tween/DMSO/water without the active compound.

After 24 hours, the plants are inoculated by spraying the leaves with an aqueous suspension of *Pyricularia oryzae* spores. The inoculated rice plants are incubated at 25° C. and a relative atmospheric humidity of 80%.

Evaluation (% efficacy) is carried out 6 days after inoculation in comparison with the control plants. 0% means an efficacy which corresponds to that of the control plants, whereas an efficacy of 100% means that no infection is observed.

In this test, the following compounds according to the invention show, at an active compound concentration of 500 ppm, an efficacy of 70% or more:

| Ex. No | Efficacy % |
|---|---|
| 1 | 100 |
| 8 | 75 |

Example T

Preventative In Vivo Test with *Puccinia recondita* (Brown Rust on Wheat)

The active compounds tested are prepared by homogenization in a mixture of acetone/Tween/DMSO and then diluted with water to the desired active compound concentration.

Wheat plants (cultivar "Scipion"), sown in a 50/50 peat/pozzolana soil substrate and cultivated at 22° C. (12 h)/20° C. (12 h), are treated at the 1-leaf stage (height 10 cm) by spraying with the active compound, prepared as above. As a control, plants are treated with the mixture of acetone/Tween/DMSO/water without the active compound.

After 24 hours, the plants are inoculated by spraying the leaves with an aqueous suspension of *Puccinia recondita* spores. The inoculated wheat plants are incubated at 20° C. and a relative atmospheric humidity of 100% for 24 hours and then for 10 days at 20° C. and a relative atmospheric humidity of 70%.

Evaluation (% efficacy) is carried out 10 days after inoculation in comparison with the control plants. 0% means an efficacy which corresponds to that of the control plants, whereas an efficacy of 100% means that no infection is observed.

In this test, the following compounds according to the invention show, at an active compound concentration of 500 ppm, an efficacy of 70% or more:

| Ex. No | Efficacy % |
|---|---|
| 1 | 100 |
| 8 | 97 |
| 9 | 86 |
| 11 | 93 |
| 12 | 93 |
| 14 | 93 |
| 15 | 100 |
| 17 | 100 |

Example U

Preventative In Vivo Test with *Septoria tritici* (Leaf Blotch Disease on Wheat)

The active compounds tested are prepared by homogenization in a mixture of acetone/Tween/DMSO and then diluted with water to the desired active compound concentration.

Wheat plants (cultivar "Scipion"), sown in a 50/50 peat/pozzolana soil substrate and cultivated at 22° C. (12 h)/20° C. (12 h), are treated at the 1-leaf stage (height 10 cm) by spraying with the active compound, prepared as above. As a control, plants are treated with the mixture of acetone/Tween/DMSO/water without the active compound.

After 24 hours, the plants are inoculated by spraying the leaves with an aqueous suspension of cryogenically preserved *Septoria tritici* spores. The inoculated wheat plants are incubated at 18° C. and a relative atmospheric humidity of 100% for 72 hours and then for 21 to 28 days at a relative atmospheric humidity of 90%.

Evaluation (% efficacy) is carried out 21 to 28 days after inoculation in comparison with the control plants. 0% means an efficacy which corresponds to that of the control plants, whereas an efficacy of 100% means that no infection is observed.

In this test, the following compounds according to the invention show, at an active compound concentration of 500 ppm, an efficacy of 70% or more:

| Ex. No | Efficacy % |
|---|---|
| 1 | 100 |
| 8 | 100 |
| 9 | 100 |
| 10 | 96 |
| 11 | 100 |
| 12 | 100 |
| 14 | 100 |
| 15 | 86 |
| 17 | 97 |

Example V

Preventative In Vivo Test with *Sphaerotheca fuliginea* (Powdery Mildew on Cucumber)

The active compounds tested are prepared by homogenization in a mixture of acetone/Tween/DMSO and then diluted with water to the desired active compound concentration.

Cucumber plants (cultivar "Vert petit de Paris"), sown in a 50/50 peat/pozzolana soil substrate and cultivated at 24° C., are treated at the Z11 cotyledon stage by spraying with the active compound, prepared as above. As a control, plants are treated with the mixture of acetone/Tween/DMSO/water without the active compound.

After 24 hours, the plants are inoculated by spraying the leaves with an aqueous suspension of *Sphaerotheca fuliginea* spores. The inoculated cucumber plants are incubated at about 20° C./25° C. and a relative atmospheric humidity of 60/70%.

Evaluation (% efficacy) is carried out 12 days after inoculation in comparison with the control plants. 0% means an efficacy which corresponds to that of the control plants, whereas an efficacy of 100% means that no infection is observed.

In this test, the following compounds according to the invention show, at an active compound concentration of 500 ppm, an efficacy of 70% or more:

| Ex. No | Efficacy % |
|---|---|
| 1 | 100 |
| 8 | 100 |
| 9 | 100 |
| 10 | 98 |
| 11 | 100 |
| 12 | 100 |
| 14 | 100 |
| 15 | 98 |
| 17 | 100 |
| 18 | 100 |

Example W

Preventative In Vivo Test with *Uromyces appendiculatus* (Bean Rust)

The active compounds tested are prepared by homogenization in a mixture of acetone/Tween/DMSO and then diluted with water to the desired active compound concentration.

Bean plants (cultivar "Saxa"), sown in a 50/50 peat/pozzolana soil substrate and cultivated at 24° C., are treated at the 2-leaf stage (height 9 cm) by spraying with the active compound, prepared as above. As a control, plants are treated with the mixture of acetone/Tween/DMSO/water without the active compound.

After 24 hours, the plants are inoculated by spraying the leaves with an aqueous suspension of *Uromyces appendiculatus* spores. The inoculated bean plants are incubated at 20° C. and a relative atmospheric humidity of 100% for 24 hours and then for 10 days at 20° C. and a relative atmospheric humidity of 70%.

Evaluation (% efficacy) is carried out 10 days after inoculation in comparison with the control plants. 0% means an efficacy which corresponds to that of the control plants, whereas an efficacy of 100% means that no infection is observed.

In this test, the following compounds according to the invention show, at an active compound concentration of 500 ppm, an efficacy of 70% or more:

| Ex. No | Efficacy % |
|---|---|
| 1 | 100 |
| 8 | 100 |
| 9 | 93 |
| 11 | 97 |
| 12 | 99 |
| 14 | 100 |
| 15 | 100 |
| 17 | 100 |
| 18 | 100 |

Example X

*Puccinia* Test (Wheat)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. One day after this treatment, the plants are inoculated with an aqueous spore suspension of *Puccinia recondita*. The plants remain in an incubation cabin at 22° C. and a relative atmospheric humidity of 100% for 48 hours. The plants are then placed in a greenhouse at a temperature of about 20° C. and a relative atmospheric humidity of about 80%.

Evaluation of the test is carried out 7-9 days after the inoculation. 0% means an efficacy which corresponds to that of the untreated control, whereas an efficacy of 100% means that no infection is observed.

TABLE

| | *Puccinia* test (wheat)/protective | |
|---|---|---|
| Active compound | Active compound application rate in ppm | Efficacy in % |
| known from EP 0087148: 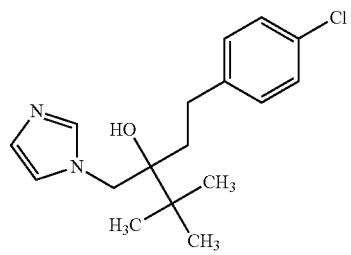 | 500 | 70 |

TABLE-continued

Puccinia test (wheat)/protective

| | Active compound | Active compound application rate in ppm | Efficacy in % |
|---|---|---|---|
| Ex. 4 | According to the invention: | 500 | 95 |

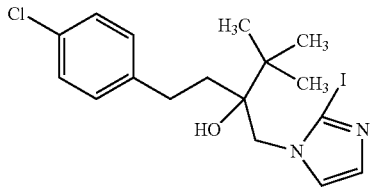

Example Y

Uromyces Test (Beans)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the bean rust pathogen (Uromyces appendiculatus) and then remain in an incubation cabin at about 20° C. and 100% relative atmospheric humidity for 1 day.

The plants are then placed in a greenhouse at about 21° C. and a relative atmospheric humidity of about 90%.

Evaluation of the test is carried out 10 days after the inoculation. 0% means an efficacy which corresponds to that of the untreated control, whereas an efficacy of 100% means that no infection is observed.

TABLE

Uromyces test (beans)/protective

| Active compound | Active compound application rate in ppm | Efficacy in % |
|---|---|---|
| known from EP 0297345: | 10 | 65 |

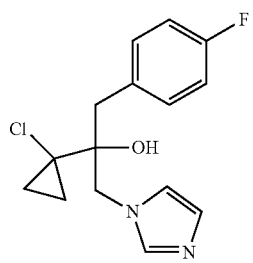

TABLE-continued

Uromyces test (beans)/protective

| | Active compound | Active compound application rate in ppm | Efficacy in % |
|---|---|---|---|
| Ex. 1 | According to the invention: | 10 | 100 |

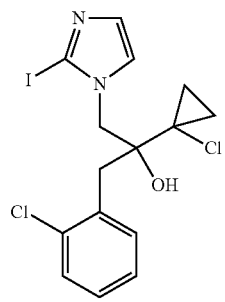

Example Z

Septoria tritici Test (Wheat)/Protective

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for protective activity, young plants are sprayed with the preparation of active compound or active compound combination at the stated application rate.

After the spray coating has dried on, the plants are sprayed with a spore suspension of Septoria tritici. The plants remain in an incubation cabin at about 20° C. and a relative atmospheric humidity of about 100% for 48 hours and then at about 15° C. in a translucent incubation cabin at a relative atmospheric humidity of about 100% for 60 hours.

The plants are then placed in a greenhouse at a temperature of about 15° C. and a relative atmospheric humidity of about 80%.

Evaluation of the test is carried out 21 days after the inoculation. 0% means an efficacy which corresponds to that of the untreated control, whereas an efficacy of 100% means that no infection is observed.

TABLE

*Septoria tritici* test (wheat)/protective

| Active compound | Active compound application rate in ppm | Efficacy in % |
|---|---|---|
| known from EP 0297345: | 250 | 43 |
| Ex. 1: According to the invention: | 250 | 86 |

The invention claimed is:

1. A 2-Iodoimidazole derivative of formula (I)

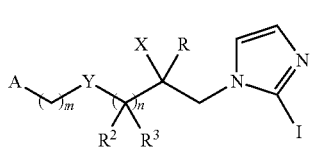

in which

X represents $OR^1$,

Y represents O, S, $SO_2$, —$CH_2$— or a direct bond, m represents 0 or 1, n represents 0 or 1, R represents in each case optionally branched $C_3$-$C_7$-alkyl, $C_1$-$C_8$-haloalkyl, $C_2$-$C_7$-alkenyl, $C_2$-$C_7$-haloalkenyl, $C_2$-$C_7$-alkynyl, $C_2$-$C_7$-haloalkynyl, $C_1$-$C_4$-alkoxy-$C_1$-$C_3$-alkyl, $C_1$-$C_4$-haloalkoxy-$C_1$-$C_3$-alkyl, tri($C_1$-$C_3$-alkyl)silyl-$C_1$-$C_3$-alkyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-haloalkylthio-, $C_1$-$C_4$-alkylthio- or phenoxy-substituted (where phenoxy may in turn be substituted by halogen or $C_1$-$C_4$-alkyl) $C_3$-$C_7$-cycloalkyl or $C_3$-$C_7$-cycloalkyl-$C_1$-$C_3$-alkyl where any substitution is on the cycloalkyl moiety, and optionally mono- to tri-halogen- or —$C_1$-$C_4$-alkyl-substituted phenyl, $R^1$ represents hydrogen, ($C_1$-$C_3$-alkyl)carbonyl, ($C_1$-$C_3$-haloalkyl)carbonyl or tri($C_1$-$C_3$-alkyl)silyl, $R^2$ represents hydrogen, fluorine, chlorine, bromine, iodine, $C_1$-$C_4$-alkyl or $C_1$-$C_4$-haloalkyl, $R^3$ represents hydrogen, fluorine, chlorine, bromine, iodine, $C_1$-$C_4$-alkyl or $C_1$-$C_4$-haloalkyl, $R^2$ and $R^3$ together may furthermore represent straight-chain or branched and optionally halogen substituted $C_2$-$C_5$-alkylene, R and $R^2$ together may furthermore represent straight-chain or branched and optionally halogen- or $C_1$-$C_4$-alkyl-substituted $C_2$-$C_5$-alkylene, R and $R^1$ together may furthermore represent optionally fluorine-, chlorine-, bromine-, $C_1$-$C_4$-alkyl- or $C_1$-$C_4$-haloalkyl-substituted —($CH_2$)$_3$—, —$CH_2$O—, —($CH_2$)$_2$O—, —($CH_2$)$_3$O—, where the oxygen of this group is in each case attached to R, such that an optionally substituted tetrahydrofuran-2-yl, 1,3-dioxetan-2-yl, 1,3-dioxolan-2-yl or 1,3-dioxan-2-yl ring is formed, $R^1$ and $R^2$ may furthermore represent a direct bond if n represents 1, Y and $R^3$ together may furthermore form a double bond if m and n both represent 1, A represents unsubstituted or mono- to tri-$Z^1$-substituted phenyl, where $Z^1$ represents halogen, cyano, nitro, OH, SH, C(alkyl)(=NOalkyl), $C_3$-$C_7$-cycloalkyl, $C_3$-$C_6$-cycloalkyl-$C_1$-$C_2$-alkyl, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $C_1$-$C_4$-alkylsulphonyloxy, formyl, $C_2$-$C_5$-alkylcarbonyl, $C_2$-$C_5$-haloalkylcarbonyl, $C_2$-$C_5$-alkoxycarbonyl, $C_2$-$C_5$-haloalkoxycarbonyl, $C_3$-$C_6$-alkenyloxy, $C_3$-$C_6$-alkynyloxy, $C_2$-$C_5$-alkylcarbonyloxy, $C_2$-$C_5$-haloalkylcarbonyloxy, trialkylsilyl, or represents in each case optionally halogen-, $C_1$-$C_4$-alkyl-, $C_1$-$C_4$-haloalkyl-, $C_1$-$C_4$-alkoxy- or $C_2$-$C_4$-alkylcarbonyl-monosubstituted phenyl, phenoxy or phenylthio, or A represents in each case mono- or poly-$Z^2$-substituted five- or six-membered heteroaryl selected from furyl, thienyl, pyrrolyl, pyrazolyl, imidazolyl, oxazolyl, thiazolyl, isoxazolyl, isothiazolyl, triazolyl, tetrazolyl, oxadiazolyl, thiadiazolyl, pyridinyl, pyridazinyl, pyrimidinyl, pyrazinyl and triazinyl, where $Z^2$ represents halogen, $C_1$-$C_4$-alkyl, $C_1$-$C_4$-alkylthio, $C_1$-$C_4$-alkoxy, $C_1$-$C_4$-haloalkyl, $C_1$-$C_4$-halothioalkyl, $C_1$-$C_4$-haloalkoxy, $C_3$-$C_7$-cycloalkyl, in each case optionally halogen- or $C_1$-$C_4$-alkyl-substituted phenyl, phenoxy or phenylthio, or an agrochemically active salt thereof.

2. The 2-iodoimidazole derivative of formula (I) of claim 1, wherein said 2-iodoimidazole derivative is

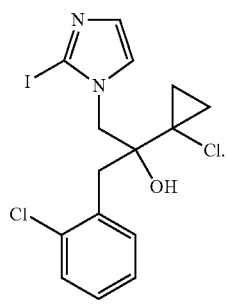 [SMILES: OC(Cc1ccccc1Cl)(Cn1ccnc1I)C1(Cl)CC1]

3. A method for controlling phytopathogenic harmful fungi, the method comprising applying a 2-iodoimidazole derivative of the formula (I) and/or salt according to claim 1 to a phytopathogenic harmful fungi.

4. A method for regulating plant growth, the method comprising applying a 2-iodoimidazole derivative of the formula (I) and/or salt according to claim 1 to a plant.

5. A method for treating a transgenic plant, the method comprising applying a 2-iodoimidazole derivative of the formula (I) and/or salt according to claim 1 to a transgenic plant.

6. A method for treating seed and/or seed of a transgenic plant, the method comprising applying a 2-iodoimidazole derivative of the formula (I) and/or salt according to claim 1 to a seed and/or a seed of a transgenic plant.

7. A composition for controlling phytopathogenic harmful fungi, comprising at least one 2-iodoimidazole derivative of the formula (I) and/or salt according to claim 1, in addition to one or more extenders and/or one or more surfactants.

8. A method for controlling phytopathogenic harmful fungi, comprising applying a 2-iodoimidazole derivative of formula (I) and/or salt according to claim 1 to phytopathogenic harmful fungi and/or a habitat thereof.

9. The method of claim 8, wherein said 2-iodoimidazole derivative is

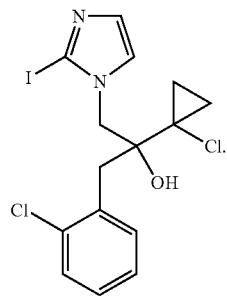 [SMILES: OC(Cc1ccccc1Cl)(Cn1ccnc1I)C1(Cl)CC1]

10. A process for producing a composition for controlling phytopathogenic harmful fungi, comprising mixing a 2-iodoimidazole derivative of formula (I) and/or salt according to claim 1 with one or more extenders and/or one or more surfactants.

* * * * *